(12) United States Patent
Kanemaru

(10) Patent No.: US 11,312,087 B2
(45) Date of Patent: Apr. 26, 2022

(54) TUBE JOINING DEVICE

(71) Applicant: TERUMO KABUSHIKI KAISHA, Tokyo (JP)

(72) Inventor: Keisuke Kanemaru, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/496,380

(22) PCT Filed: Mar. 23, 2018

(86) PCT No.: PCT/JP2018/010537
§ 371 (c)(1),
(2) Date: Sep. 20, 2019

(87) PCT Pub. No.: WO2018/173957
PCT Pub. Date: Sep. 27, 2018

(65) Prior Publication Data
US 2020/0047423 A1    Feb. 13, 2020

(30) Foreign Application Priority Data

Mar. 24, 2017    (JP) .............................. JP2017-059278

(51) Int. Cl.
*B29C 65/18*    (2006.01)
*B29C 65/74*    (2006.01)
(Continued)

(52) U.S. Cl.
CPC ............ *B29C 65/743* (2013.01); *B29C 65/18* (2013.01); *B29C 65/7802* (2013.01);
(Continued)

(58) Field of Classification Search
CPC ...... A61M 39/146; A61M 39/18; A61M 1/28; A61M 2205/3368; A61M 2205/3372; A61M 2205/36; A61M 2205/6081; B29C 65/20; B29C 65/2046; B29C 65/743; B29C 65/7802; B29C 65/7841; B29C 66/0018; B29C 66/1142; B29C 66/5221; B29C 66/71; B29C 66/7373; B29C 66/73921;
(Continued)

(56) References Cited

U.S. PATENT DOCUMENTS 5,802,689 A * 9/1998 Sano ..................... B29C 66/857
29/33 T
6,026,882 A * 2/2000 Yamada ............. A61M 39/146
156/433
(Continued)

FOREIGN PATENT DOCUMENTS

JP    2013-146354 A    8/2013
JP    2013146354 A  *  8/2013    ......... B29C 66/5221

*Primary Examiner* — Michael A Tolin
(74) *Attorney, Agent, or Firm* — Sheridan Ross P.C.

(57) ABSTRACT

A tube joining device includes a delivery with a first pusher member providing forward movement and backward movement along a delivery direction and delivering a wafer to a first position between a take-out position and a stand-by position, and with a second pusher member providing forward movement and backward movement along the delivery direction in combination with the first pusher member, and the wafer from the first position to the stand-by position.

20 Claims, 17 Drawing Sheets

(51) Int. Cl.
B29C 65/78 (2006.01)
B29C 65/00 (2006.01)
B29L 23/00 (2006.01)

(52) U.S. Cl.
CPC .......... B29C 66/5221 (2013.01); B29C 66/90 (2013.01); *B29L 2023/00* (2013.01)

(58) Field of Classification Search
CPC ............ B29C 66/8221; B29C 66/8227; B29C 66/857; B29C 66/90; B29C 65/18; B29C 65/203; B29C 65/2076; B29C 65/30; B29C 66/002; B29C 66/81812; B29C 66/8618; B29C 66/8748; B29C 66/91921; B29C 66/9672; B29C 66/9674; B29L 2023/007; B29L 2023/00; B29K 2027/06
See application file for complete search history.

(56) References Cited

U.S. PATENT DOCUMENTS

| | | | | |
|---|---|---|---|---|
| 6,460,592 | B1 * | 10/2002 | Sano | .................... A61M 39/146 |
| | | | | 156/503 |
| 6,463,979 | B1 * | 10/2002 | Sano | .................... B29C 65/7841 |
| | | | | 156/503 |
| 8,857,485 | B2 * | 10/2014 | Buhler | .............. B29C 66/73921 |
| | | | | 156/353 |
| 2002/0174956 | A1 * | 11/2002 | Sano | .................... B29C 66/857 |
| | | | | 156/503 |

\* cited by examiner

TUBE JOINING DEVICE

TECHNICAL FIELD

The present invention relates to a tube joining device that is used in joining of a tube.

BACKGROUND ART

As a technology of connecting tubes formed from a resin to each other, there has been known a joining method in which ends of the tubes formed from a resin are fused and the fused ends are pressed for pressure-joining. The technology has been widely used in various industrial fields, and as an example thereof, an application to a medical technology such as a peritoneal dialysis method has been attempted.

The peritoneal dialysis method is a method in which a predetermined dialysis fluid is put into a body by using a tube (catheter) that is inserted into the abdominal cavity of a patient, and water or waste matters which are transferred to the dialysis fluid through the peritoneum are removed to the outside of the body. When putting the dialysis fluid into the body, the tube that is inserted into the patient is liquid-tightly joined to a tube of a bag in which the dialysis fluid is accommodated. In addition, even when discharging the dialysis fluid from the inside of the body, the tube inserted into the patient is liquid-tightly joined to a tube of a liquid discharge bag.

As described above, one tube that becomes a joining target is inserted into the abdominal cavity of the patient. Accordingly, during joining work, it is necessary to pay the closest attention to the work in order for each tube not to be contaminated. In consideration of such circumstances, for example, as described in Patent Literature 1, a tube joining device capable of automatically performing joining in an aseptic condition by fusing two tubes formed from a resin is developed. In the device, fused ends of the two tubes are replaced and joined, and thus there is no concern of bacterium contamination during joining, and it is possible to maintain sterilization of the tube, the dialysis fluid in the bag, and the like. In addition, in the device, the two tubes are superimposed in an upper and lower direction (height direction) of the device and are set to a close contact state, and a plate-shaped metal wafer that is heated is moved to approach the tubes to perform fusing.

CITATION LIST

Patent Literature

Patent Literature 1: JP 2013-146354 A

SUMMARY OF INVENTION

Technical Problem

In the tube joining device, when initiating fusing-joining work of tubes, a wafer (plate-shaped cutting member) that is set in the tube joining device is moved to a predetermined stand-by state. A movement distance of the wafer in the tube joining device is lengthened as a distance from a cassette in which the wafer is stored to the stand-by position increases.

The tube joining device is provided with a delivery mechanism (delivery device) that performs work of delivering the wafer. Dimensions or an operation range of constituent members of the delivery mechanism are determined depending on a movement distance of the wafer. Accordingly, as the movement distance of the wafer is set to longer, the size of the delivery mechanism increases. However, an increase in size of the tube joining device is limited, and thus the increase in size of the delivery mechanism is also limited. According to this, it is necessary for the movement distance of the wafer to be set within a constant range that does not have a great influence on a device design. According to this, the degree of freedom of the device design (layout of a device configuration) is greatly limited.

The invention has been made in consideration of the above-described problems, and an object thereof is to provide a tube joining device in which the degree of freedom of device design is improved.

Solution to Problem

To accomplish the object, according to an aspect of the invention, there is provided a tube joining device that fuses an end of a first tube and an end of a second tube by a plate-shaped cutting member that is heated, and replaces the fused end of the first tube and the fused end of the second tube and joins the fused ends in an aseptic condition. The tube joining device includes: a housing in which the first tube and the second tube are set; a cassette mounting portion to which a cassette that stores the cutting member is detachably mounted; a control unit that performs operation control; and a delivery mechanism that delivers the cutting member accommodated in the cassette to a stand-by position, at which the cutting member stands by, by a command of the control unit when fusing the first tube and the second tube. The delivery mechanism includes a first pusher member that is provided to perform forward movement and backward movement along a delivery direction and delivers the cutting member to a first position that is set between a eject position at which the cutting member is taken out from the cassette and the stand-by position, and a second pusher member that is provided to perform forward movement and backward movement along the delivery direction in combination with the first pusher member, and delivers the cutting member from the first position to the stand-by position. An operation of delivering the cutting member by the first pusher member is capable of being switched to an operation of delivering the cutting member by the second pusher member in synchronization with forward movement and backward movement of the first pusher member and the second pusher member.

Advantageous Effects of Invention

According to the tube joining device configured as described above, it is possible to switch an operation of delivering the cutting member by the first pusher member to an operation of delivering the cutting member by the second pusher member. According to this, it is possible to shorten a movement distance of the delivery mechanism when delivering the cutting member from the eject position to the stand-by position. Accordingly, it is possible to provide a tube joining device in which the degree of freedom of device design is improved.

BRIEF DESCRIPTION OF DRAWINGS

FIGS. 17A to 17B are views illustrating the tubes after joining, in which FIG. 17A is an enlarged view of the tubes after joining, and FIG. 17B is a view schematically illustrating an installation state of the tubes after joining.

DESCRIPTION OF EMBODIMENTS

Figure 1:
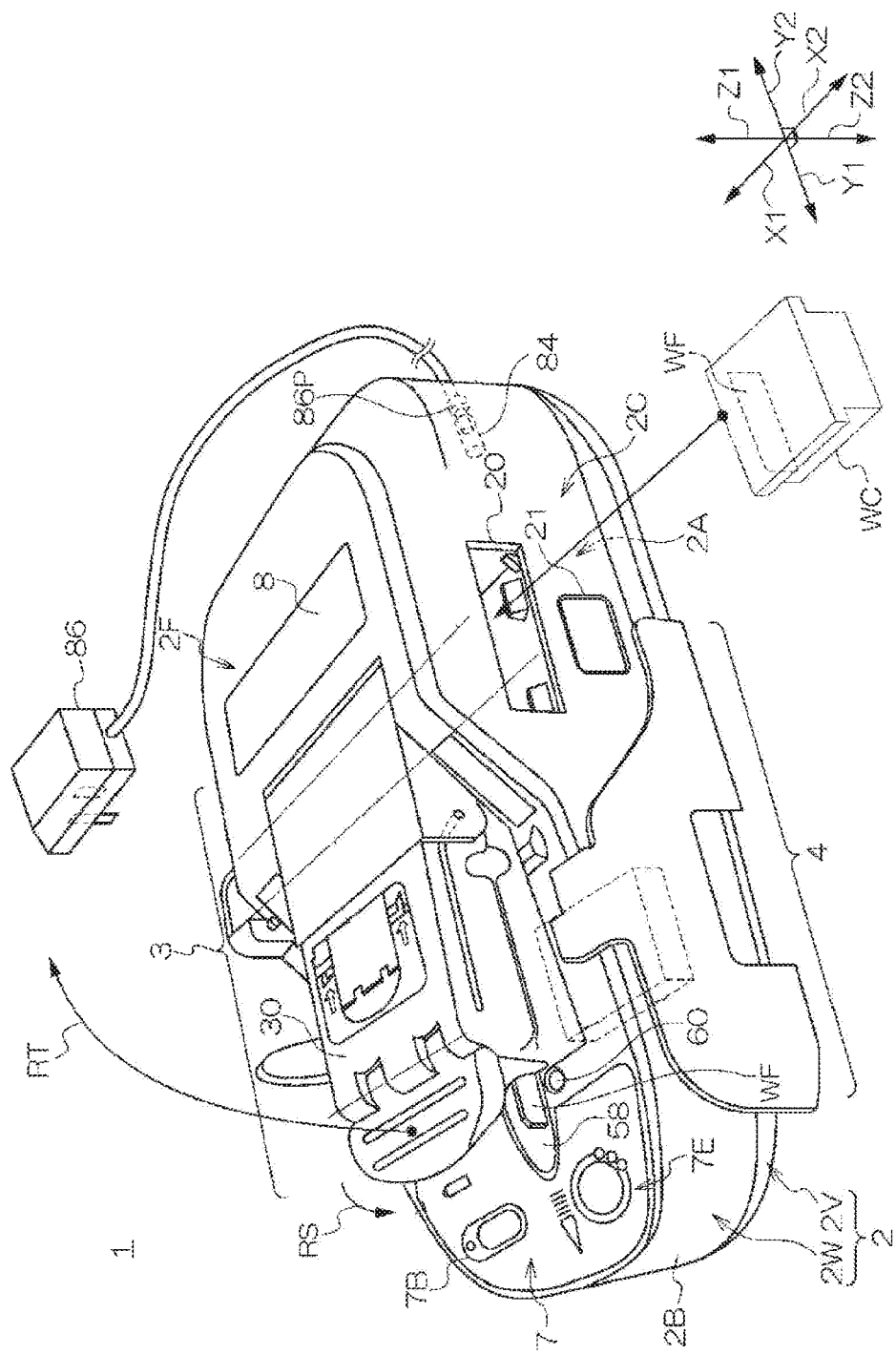
FIG. 1 is a perspective view illustrating a tube joining device according to an embodiment of the invention.

Hereinafter, an embodiment of the invention will be described with reference to the accompanying drawings. Furthermore, dimension ratios in the drawings are exaggerated for convenience of explanation, and may be different from actual ratios.

FIG. 1 is an overview perspective view illustrating a tube joining device 1 according to this embodiment.

The tube joining device 1 fuses ends of a plurality of tubes T1 and T2 (hereinafter, referred to as a first tube T1 and a second tube T2), and presses and joins the fused ends in an aseptic condition. In this embodiment, description will be given of the tube joining device with reference to an example that is applied to a medical device that is used in joining of a dialysis fluid tube (corresponding to the first tube T1) of a peritoneal dialysis fluid bag, and a peritoneal catheter side tube (corresponding to the second tube T2), which is used when performing peritoneal dialysis, of a patient (refer to FIG. 15).

As illustrated in FIGS. 16A to 16D and FIGS. 17A to 17B, the tube joining device 1 has a configuration in which an end of the first tube T1 and an end of the second tube T2 are fused by a heated wafer WF (corresponding to a plate-shaped cutting member), and replaces and joins the fused end of the first tube T1 and the fused end of the second tube T2.

Respective configurations of the tube joining device 1 will be described.

For example, a preferred use environment of the tube joining device 1 is an environmental temperature of 10° C. to 40° C. and a relative humidity of 30% to 85%. However, the use environment is not particularly limited as long as the ends of the tubes T1 and T2 can be pressure-welded.

As illustrated in FIG. 1, for example, the tube joining device 1 includes a housing 2 in which the first tube T1 and the second tube T2 are set, a wafer cassette storage unit 82 (corresponding to a cassette mounting unit) in which wafer cassette WC (corresponding to a cassette) storing the wafer WF is detachably mounted, a control unit 100 that performs operation control, and a delivery mechanism 500 that delivers the wafer WF stored in the wafer cassette WC to a stand-by position PS3 at which the wafer WF stands by, by a command of the control unit 100 when fusing the first tube T1 and the second tube T2.

For example, the housing 2 has a size of 135 mm (width)×99 mm (height)×268 mm (depth), and a weight of approximately 2.4 kg.

The housing 2 includes an upper side housing portion 2W, and a lower side housing portion 2V that is combined to the upper side housing portion 2W.

A tube setting assisting tool 4 is detachably attached to the housing 2. The housing 2 and the tube setting assisting tool 4 are formed from, for example, a hard plastic, but there is no particular limitation to a material, and the like.

As described later, the housing 2 accommodates respective constituent elements of the tube joining device 1. The clamp cover section 3 is disposed on an upper portion of the housing 2.

For example, the housing 2 can be set to a bright color with a relatively high luminosity, specifically, a cream color or a white color. In addition, for example, the tube setting assisting tool 4 may be set to an orange color so that a user (a person who actually uses the tube joining device, a patient, or the like) can visually clearly distinguish the housing 2 and the tube setting assisting tool 4. However, colors of the respective units are not particularly limited, and may be arbitrarily selected.

Figure 4:
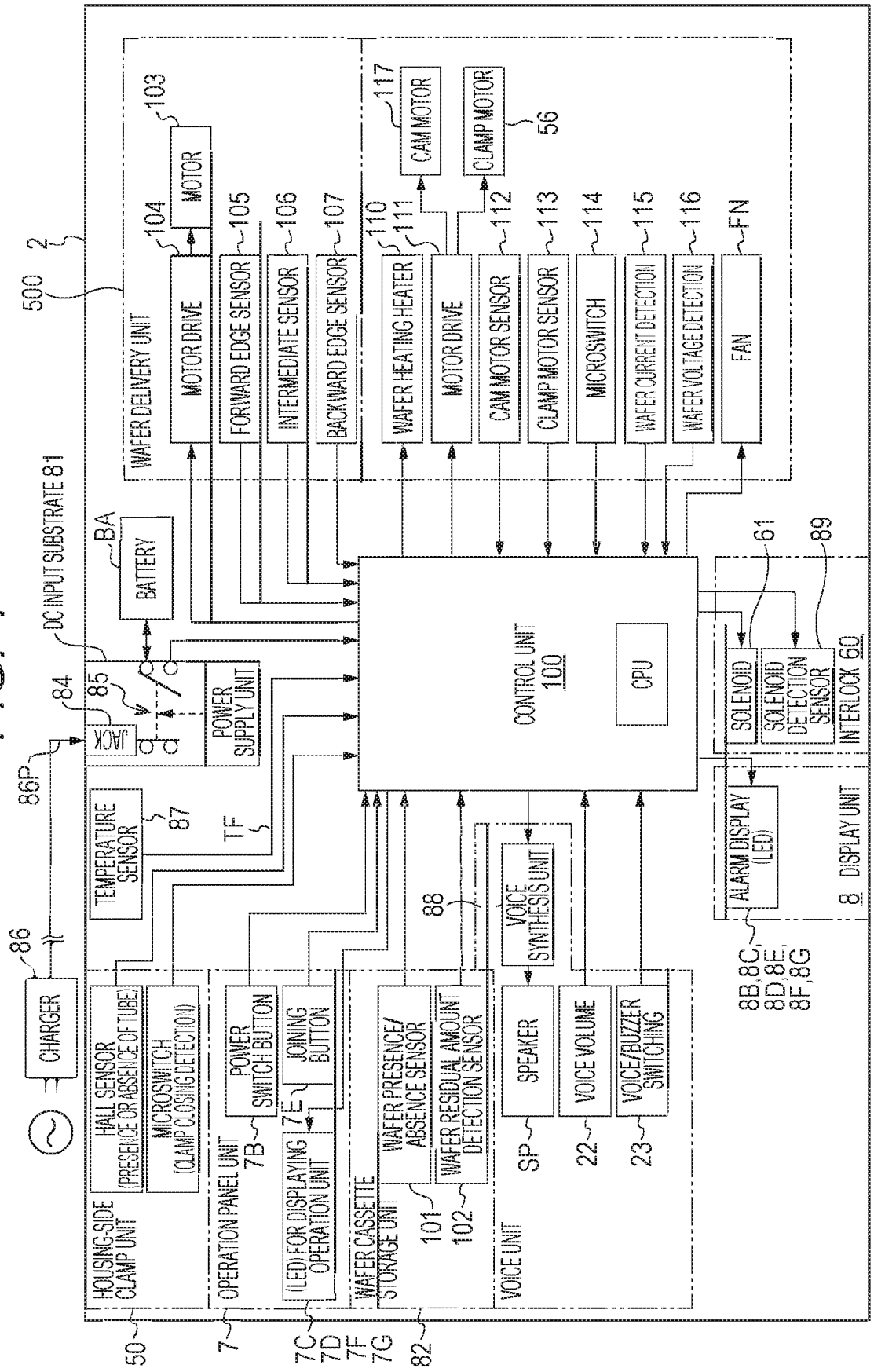
FIG. 4 is a view illustrating an electric block of a control system of the tube joining device.

A speaker SP that emits sound and a fan FN that discharges a gas inside the housing 2 are disposed on a bottom surface portion 2A of the housing 2 (refer to FIG. 4). The fan FN also has a function as a cooling fan that cools down the wafer WF after terminating a joining operation. In the bottom surface portion of the housing 2, a voice opening that outputs a voice guidance, an alarm sound, and the like which are emitted from the speaker SP to the outside of the housing 2 may be provided, or an exhaust opening for compulsorily discharging heat generated inside the housing 2 or a gas that passes through the inside of the housing 2 to the outside of the housing 2 when the cooling fan FN is operated may be provided.

Next, description will be given of an operation panel unit 7 and a display unit 8 with references to FIGS. 2A to 2B.

Figure 2A:
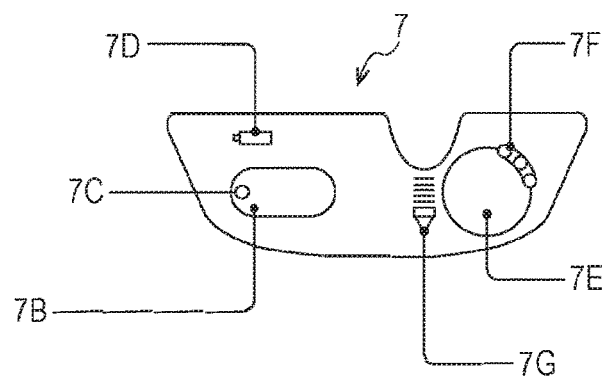
FIG. 2A is a view illustrating a configuration example of an operation panel unit that is provided on a front surface portion side of a housing illustrated in FIG. 1.

FIG. 2A illustrates the operation panel unit 7 that is provided on a front surface 2B side of the housing 2 illustrated in FIG. 1. FIG. 2B illustrates the display unit 8 that is provided on an upper surface portion 2F of the housing 2 illustrated in FIG. 1.

The operation panel unit 7 illustrated in FIG. 2A includes a [power] switch button 7B, [power] lamp 7C, a [in-charging] lamp 7D, a [joining] button 7E, a [joining] lamp 7F, and a [wafer ejecting] lamp 7G.

The [power] lamp 7C, the [in-charging] lamp 7D, the [joining] lamp 7F, and the [wafer ejecting] lamp 7G are display lamps indicating various states in the operation panel unit 7. For example, the respective lamps can be constituted by a green light-emitting diode (LED) lamp.

The [power] switch button 7B is a button that is pressed to supply power to the tube joining device 1. The [power] lamp 7C is lightened when pressing the [power] switch button 7B.

The [joining] button 7E is a button that is pressed when a user initiates fusing-joining work of fusing ends of the tubes T1 and T2 and replacing and pressure-joining the ends of the tubes T1 and T2. The [joining] lamp 7F is lightened when the [joining] button 7E is pressed. In addition, the [joining] lamp 7F may be configured to be flickered to give an alarm of a failure state to a user at the time of failure of the tube joining device 1.

Figure 3:
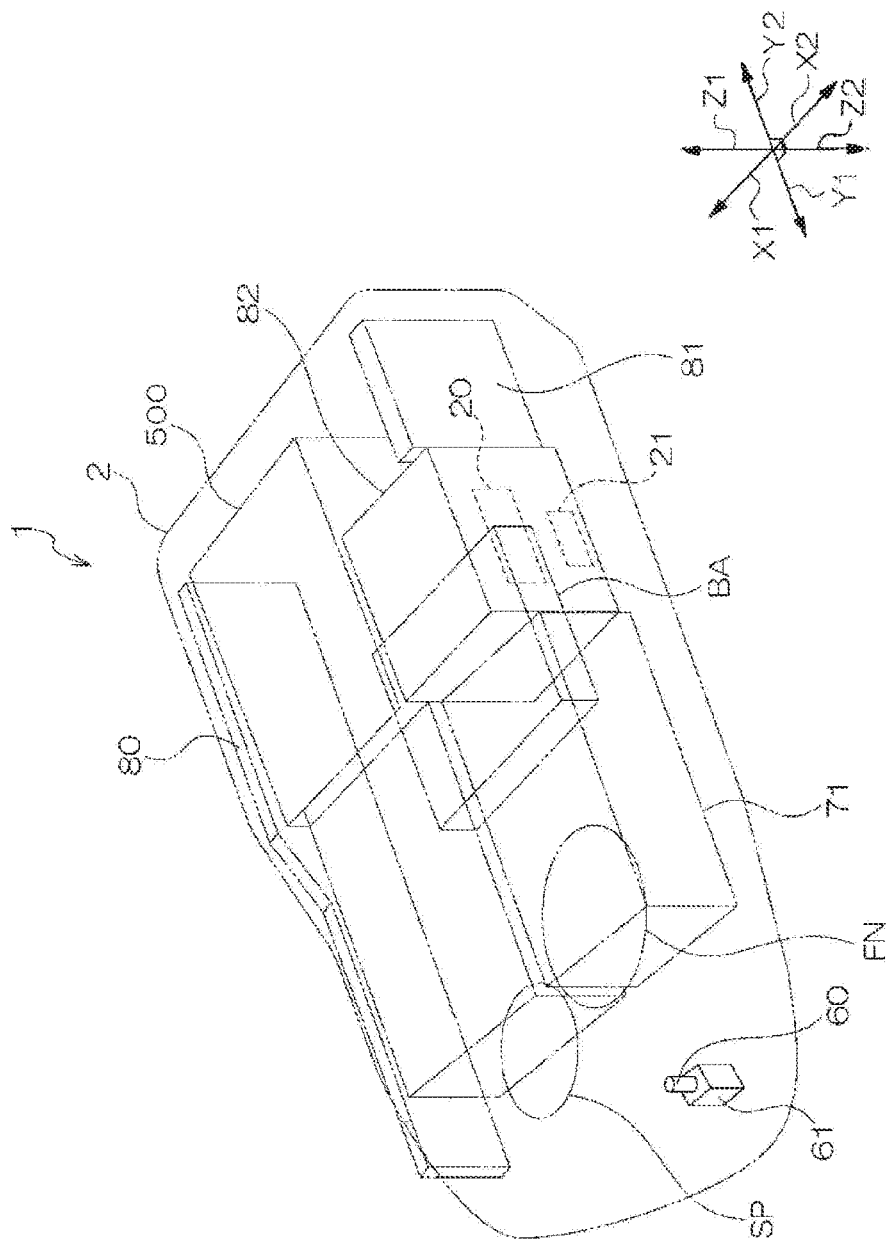
FIG. 3 is a perspective view illustrating a schematic arrangement example of constituent elements which are disposed in the housing of the tube joining device.

The [in-charging] lamp 7D is lightened in a case where charging with respect to a battery BA illustrated in FIG. 3 from a commercial AC power side is performed.

The [wafer ejecting] lamp 7G is lightened or flickered when joining between the tubes T1 and T2 is terminated, and it enters a state in which a user can take out and discharge the wafer WF that has been used from the housing 2.

Figure 2B:
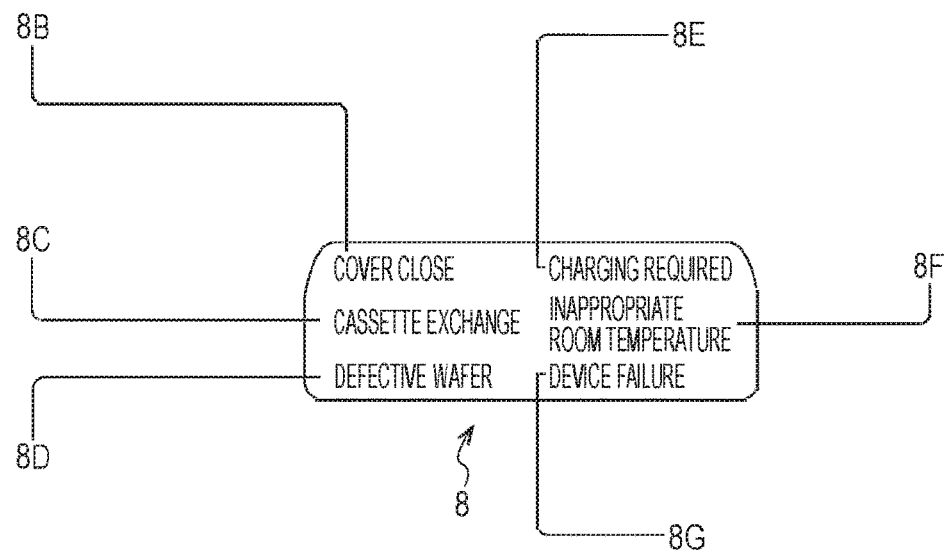
FIG. 2B is a view illustrating a configuration example of a display unit that is provided on a top surface portion of the housing illustrated in FIG. 1.

The display unit 8 illustrated in FIG. 2B includes a [cover close] lamp 8B, a [wafer cassette exchange] lamp 8C, a [defective wafer] lamp 8D, a [charging required] lamp 8E, an [inappropriate room temperature] lamp 8F, and a [device failure] lamp 8G.

The [device failure] lamp 8G is an alarm lamp that gives a notification of failure of the tube joining device 1. For example, the [device failure] lamp 8G can be constituted by a red LED lamp. The other lamps are constituted as an alarm display lamp, and can be constituted by, for example, a yellow LED lamp.

When referring to FIG. 1 again, a wafer cassette insertion portion 20 and a wafer cassette ejecting button 21 are provided on a lateral surface portion 2C of the housing 2.

The wafer cassette insertion portion 20 is constituted by a rectangular opening for inserting a wafer cassette WC illustrated in FIG. 1 in a detachable manner. In a state in which the wafer cassette WC is inserted into the housing 2 through the wafer cassette insertion portion 20, when a user pushes the wafer cassette ejecting button 21 with a finger, the wafer cassette WC can be taken out to the outside of the housing 2 through the wafer cassette insertion portion 20. The wafer cassette WC is constituted by a container which stores a plurality of wafers WF which are used in fusing of the tubes T1 and T2.

Next, the tubes T1 and T2 which become a joining target will be described.

Figure 15:
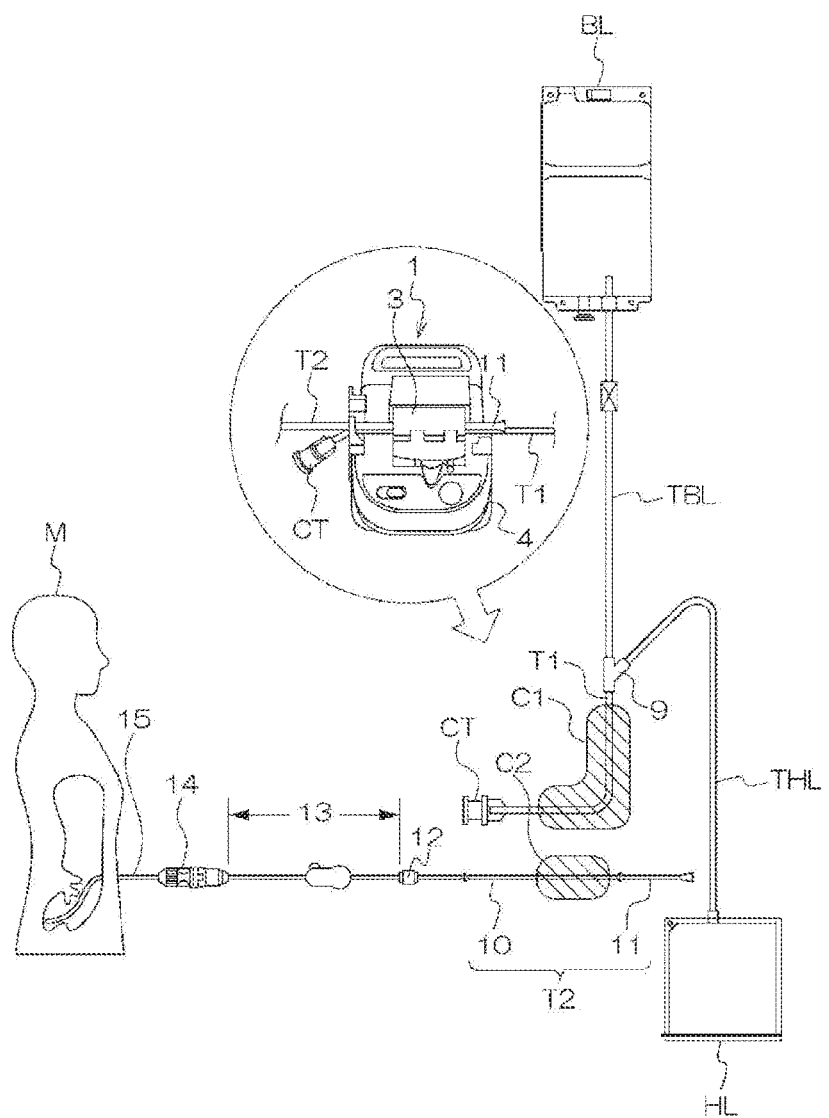
FIG. 15 is a view schematically illustrating tubes which are joined by the tube joining device according to the embodiment.

FIG. 15 illustrates two tubes T1 and T2 which are joined by the tube joining device 1. As the tube T1 and T2, for example, a vinyl chloride tube can be selected. However, the material of the tubes T1 and T2 is not limited as long as the tubes T1 and T2 can be joined to each other through fusing and pressing. For example, materials of the tubes T1 and T2 may be different from each other.

As illustrated in FIG. 15, a predetermined connector CT is attached to a tip end of the first tube T1. The first tube T1 is connected to a dialysis fluid tube TBL of a dialysis fluid bag BL through a diverging tube 9. In addition, the first tube T1 is connected to a fluid discharge tube THL of a fluid discharge bag HL through the diverging tube 9.

The tube T2 includes an extension tube 10 and a protection tube 11. The extension tube 10 is connected to a peritoneal catheter 15 through a connection tube 12, a silicone tube 13, and a catheter joint 14. One end side of the peritoneal catheter 15 is inserted into an abdominal cavity of a patient M.

Figure 16A:
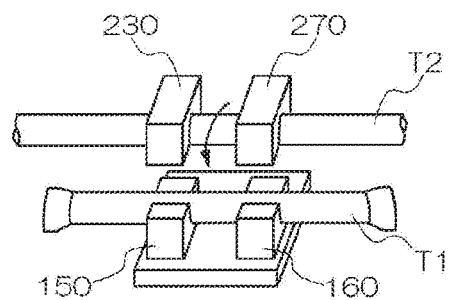
FIGS. 16A, 16B, 16C, and 16D are views schematically illustrating respective processes of fusing-joining work by the tube joining device.
Figure 16B:
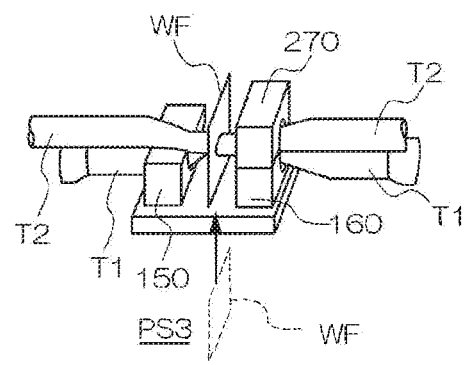

The tube joining device 1 fuses a joining portion C1 of the first tube T1 and a joining portion C2 of the second tube T2 by using a heated wafer WF in a state in which the first tube T1 and the second tube T2 are superimposed on each other (refer to FIGS. 16A and 16B. In addition, after the fusing, a fused end of the first tube T1 and a fused end of the second tube T2 are replaced, and the ends are pressed and joined (refer to FIGS. 16C and 16D.

Figure 6:
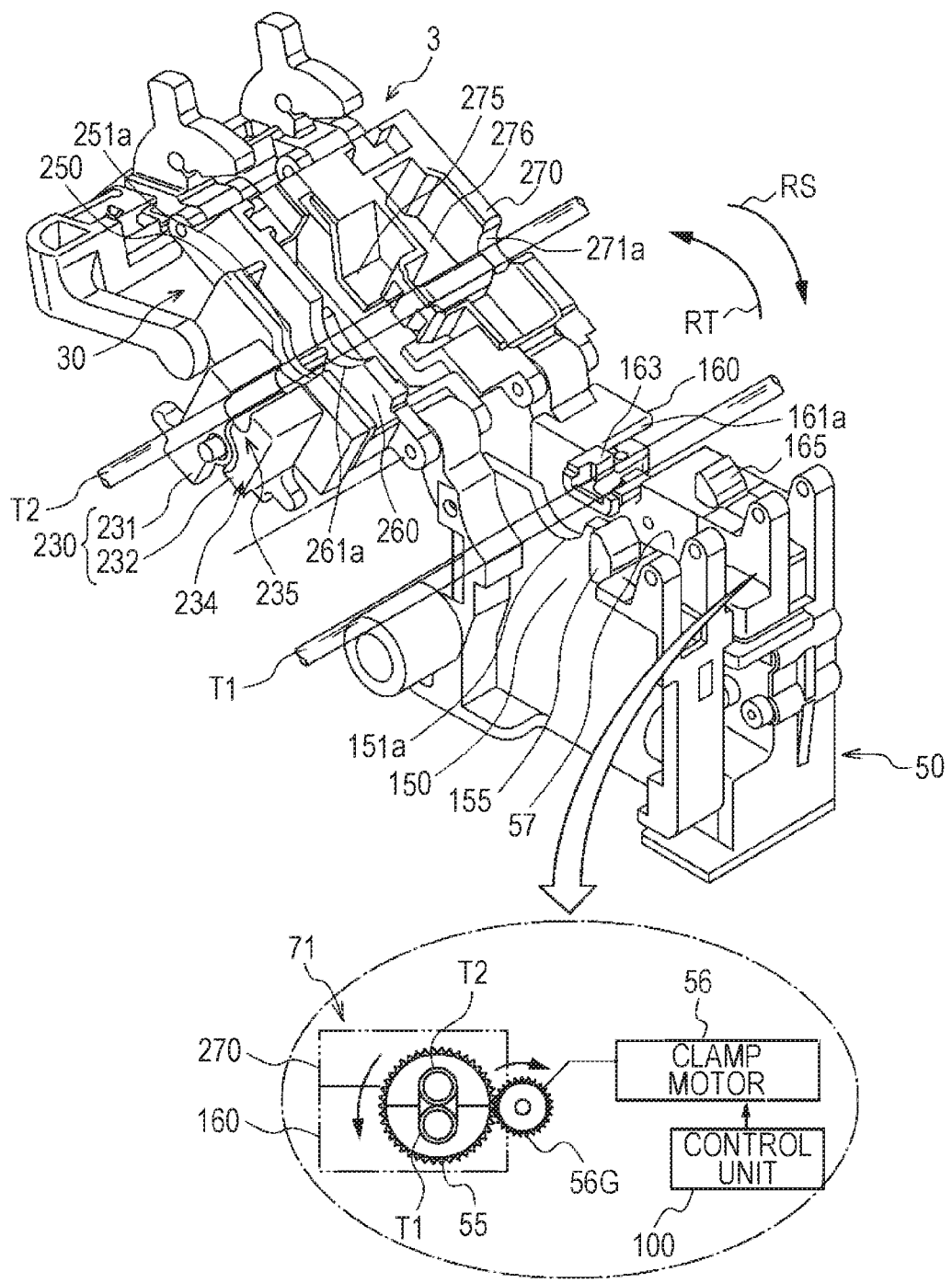
FIG. 6 is a perspective view illustrating main portions of the tube joining device in a state in which a clamp cover section is opened.

In addition, as illustrated in FIG. 6, before carrying out the joining work by the tube joining device 1, the first tube T1 and the second tube T2 are held in a housing-side clamp unit 50 provided in the housing 2 so as not to cause a positional deviation. In a state in which the tubes T1 and T2 are held in the tube joining device 1, through work of closing the clamp cover section 3 (work of causing the clamp cover section 3 to relatively approach the housing 2), the tubes T1 and T2 are set in a superimposing state in which the second tube T2 is set to an upper side and the first tube T1 is set to a lower side (refer to FIGS. 16A and 16B. After the setting, the tubes T1 and T2 are fused by using a predetermined heated wafer WF. Details of the structure of holding the tubes T1 and T2 will be described later.

As illustrated in FIG. 1, a take-out port 58 through which the wafer WF that has been used in the fusing is delivered is provided in the vicinity of the operation panel unit 7 of the housing 2. The take-out port 58 is disposed on an extended line of a predetermined gap 57 (refer to FIG. 6) through which the wafer WF passes. Since the take-out port 58 is provided on the extended line of the gap 57, a user can easily take out the wafer WF that is guided to the take-out port 58 by pinching the wafer WF with fingers. An interlock 60 that maintains a closed state of the clamp cover section 3 and a detection sensor 89 which detects an opened or closed state of the clamp cover section 3 during fusing and joining the tubes T1 and T2 are provided in the vicinity of the take-out port 58 (refer to FIG. 4).

FIG. 3 is a perspective view illustrating a schematic arrangement example of constituent elements which are disposed in the housing 2 of the tube joining device 1.

As illustrated in FIG. 3, a main substrate 80, a DC input substrate 81, a wafer cassette storage unit 82, a delivery mechanism 500, a movable clamp unit 71, a solenoid 61, the speaker SP, the fan FN, and a battery BA are accommodated in the housing 2.

For example, it is preferable that the DC input substrate 81 is disposed at a position spaced away from the main substrate 80 as much as possible. The reason for this is to prevent noise from the DC input substrate 81 from having an effect on circuit elements mounted on the main substrate 80.

The wafer cassette WC is stored in the wafer cassette storage unit 82. Detailed configurations of the wafer cassette storage unit 82 and the wafer cassette WC will be described later.

The delivery mechanism 500 is a unit that linearly moves the wafer WF in the wafer cassette WC to a predetermined stand-by position PS3 (refer to FIG. 16B. A detailed configuration of the delivery mechanism 500 will be described later.

Next, a function of a control unit 100 of the tube joining device 1 will be described with reference to FIG. 4. FIG. 4 illustrates an electric block of the tube joining device 1.

The tube joining device 1 includes a control unit 100 that collectively controls operations of respective units of the device. The control unit 100 includes a CPU such as a microcomputer, a ROM that stores a control program of the entirety of the device which is executed by the CPU or various pieces of data, and a RAM that temporarily stores measurement data or various pieces of data as a work area.

The control unit 100 is supplied with power from the battery BA on the DC input substrate 81 side. The DC input substrate 81 includes a jack 84 and a switching switch 85. When being connected to a connection pin 86P of a charger 86, the jack 84 receives a predetermined DC power that is AC/DC converted from a commercial AC power supply. Furthermore, the charger 86 and the jack 84 are also illustrated in FIG. 1.

The switching switch 85 connects the jack 84 and the battery BA. DC power from the charger 86 can be used in charging of the battery BA. In addition, the DC power charged in the battery BA is supplied to the control unit 100.

A temperature sensor 87 such as a thermistor is electrically connected to the control unit 100. The temperature sensor 87 detects an environment temperature (outside air temperature) around the housing 2, and supplies outside air temperature information TF to the control unit 100. When heating the tubes T1 and T2, the control unit 100 refers to the outside air temperature information TF, and for example, in a case where the outside air temperature is lower than a temperature that is determined in advance, the control unit 100 executes processing of lengthening a heating time of the tubes T1 and T2. In addition, for example, the control unit 100 performs operation control so that a user is notified of the environment temperature with the speaker SP.

As illustrated in FIG. 4, the [power switch] button 7B, the [joining] button 7E, and the lamps 7C, 7D, 7F, and 7G of the operation panel unit 7 which are illustrated in FIG. 2A are electrically connected to the control unit 100.

The speaker SP is electrically connected to the control unit 100 through a voice synthesis unit 88. The speaker SP emits, for example, a voice guidance that is determined in advance in accordance with a command of the control unit 100.

A voice adjusting volume 22 and a voice/message switching switch 23 are electrically connected to the control unit 100. In a case where the voice/message switching switch 23 is "turned on", a voice guidance can be emitted from the speaker SP, and in a case where the voice/message switching switch 23 is "turned off", it is possible to sound a buzzer (not illustrated).

As illustrated in FIG. 4, the [cover close] button 8B, the [wafer cassette exchange] lamp 8C, the [defective wafer] lamp 8D, the [charging required] lamp 8E, the [inappropriate room temperature] lamp 8F, and the [device failure] lamp 8G of the display unit 8 illustrated in FIG. 2B are configured to be lightened or flickered in accordance with a command of the control unit 100.

The control unit 100 controls an operation of the interlock 60 to switch a locked state or an unlocked state of the clamp cover section 3 from each other.

The wafer cassette storage unit 82 includes a wafer presence/absence sensor 101 and a wafer residual amount detection sensor 102. The wafer presence/absence sensor 101 is a sensor that detects whether or not the wafer WF remains in the wafer cassette WC illustrated in FIG. 1. The wafer residual amount detection sensor 102 is a sensor that detects how many sheets of wafers WF remain in the wafer cassette WC illustrated in FIG. 1, that is, the number of sheets of remaining wafer WF. As the wafer presence/absence sensor 101 and the wafer residual amount detection sensor 102, for example, a known photosensor or the like can be used.

The delivery mechanism 500 is a unit that linearly moves the wafer WF in the wafer cassette WC to a predetermined stand-by position PS3 (refer to FIG. 16B). As illustrated in FIG. 4, the delivery mechanism 500 includes a motor 103, a motor drive 104, a forward edge sensor 105, an intermediate sensor 106, and a backward edge sensor 107. When receiving a command from the control unit 100, the motor drive 104 drives the motor 103, and linearly moves the wafer in the wafer cassette WC to the stand-by position PS3 sheet by sheet.

The control unit 100 is electrically connected to a wafer heating heater 110, a motor drive 111, a cam motor sensor 112, a clamp motor sensor 113, a microswitch 114, a wafer current detection unit 115, a wafer voltage detection unit 116, and the fan FN. When the motor drive 111 receives a command from the control unit 100, the motor drive 111 drives the cam motor 117 or the clamp motor 56 to fuse and join the tubes T1 and T2.

The cam motor 117 performs an operation of vertically moving the wafer WF, and an operation of pressing the two tubes T1 and T2 against each other. The operation of vertically moving the wafer WF by the cam motor 117 is an operation of ascending the wafer WF from the stand-by position PS3 to a fusing position PSm on an upward side of the stand-by position PS3, and descending the wafer WF from the fusing position PSm to the stand-by position PS3 in a contrast manner (refer to FIGS. 16C and 16D. In addition, the cam motor 117 performs an operation of pressing the tubes T1 and T2 against each other after fusing the tubes T1 and T2. The pressing operation is an operation of causing the wafer WF to enter a stand-by state by descending the wafer WF from the fusing position PSm to the stand-by position PS3, and of pressing and joining the fused end of the first tube T1 and the fused end of the second tube T2 by pressing each of the fused ends against a counterpart fused end.

The clamp motor 56 performs rotation of the movable clamp unit 71 by 180° and returning rotation after the rotation by 180° (refer to FIG. 6).

The cam motor sensor 112 is constituted by, for example, a photosensor that detects a cam position and the original point. The clamp motor sensor 113 is constituted by, for example, a photosensor that detects the original point during rotation of the movable clamp unit 71.

The wafer heating heater 110 is provided to heat a wafer in accordance with a command from the control unit 100. When supplying power, the wafer current detection unit 115 detects a wafer current value that is supplied to the wafer. In addition, the wafer voltage detection unit 116 detects a wafer voltage value that is supplied to the wafer.

Next, the wafer cassette storage unit 82 and the wafer cassette WC will be described with reference to FIGS. 5A to 5B.

Figure 5A:
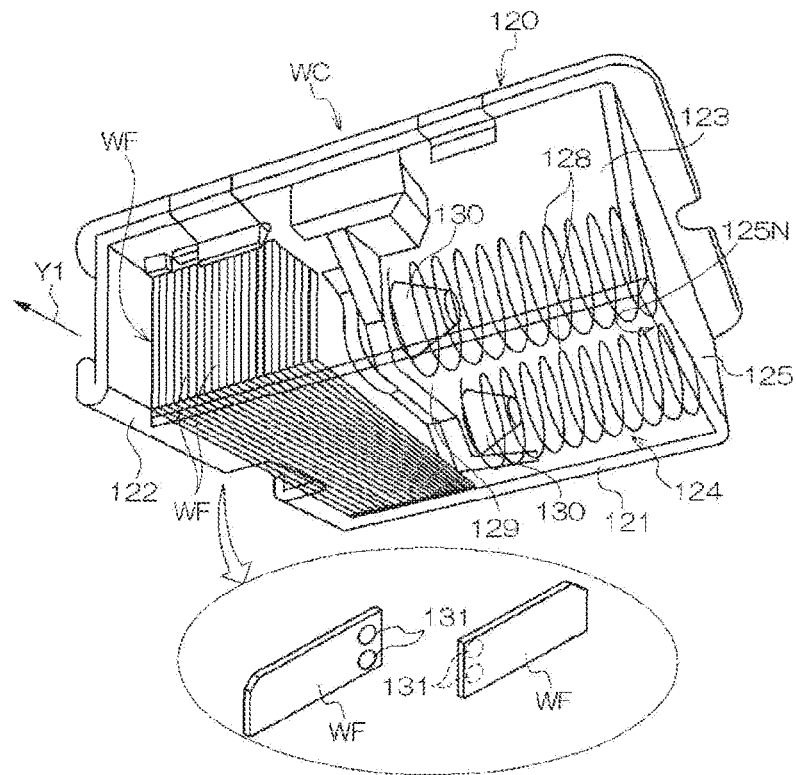
FIG. 5A is a perspective view illustrating a bottom surface portion of a wafer cassette.
Figure 5B:
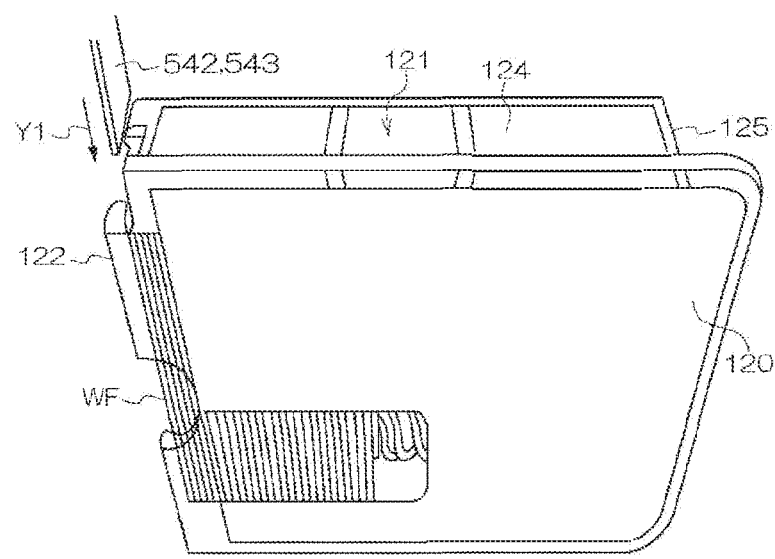
FIG. 5B is a perspective view illustrating a top surface portion of the wafer cassette.

As illustrated in FIGS. 5A and 5B, the wafer cassette WC is constituted by a container for accommodating a plurality of sheets of the wafers WF. The wafer cassette WC is preferably formed from a transparent plastic to visually confirm an inner side of the wafer WF.

As illustrated in FIG. 5A, the wafer cassette WC includes a top surface portion 120, a bottom surface portion 121, a front surface portion 122, lateral surface portions 123 and 124, and a rear surface portion 125.

The wafer WF is disposed sheet by sheet on an inner side of the front surface portion 122. In addition, as illustrated in FIG. 5B, when pressing a pusher member 542 or 543 for pushing with respect to the wafer WF in a Y1 direction, one sheet of wafer WF is pushed out sheet by sheet from the inside of the wafer cassette WC to a predetermined stand-by position along the Y1 direction.

As illustrated in FIGS. 5A and 5B, two springs 128 and a spring accommodation member 129 are accommodated at the inside of the wafer cassette WC. One end of each of the two springs is supported to an inner surface of the rear surface portion 125 of the wafer cassette WC. On the other hand, the other end of each of the two springs is supported to the spring accommodation member 129. The spring accommodation member 129 includes a positional deviation preventing portion 130 in order for each of the springs 128 not to deviate.

The two springs 128 press a plurality of sheets of the wafers WF against an inner surface of the front surface portion 122 through the spring accommodation member 129. In a state in which the wafers WF are held by the two springs 128, when the pusher member 542 or 543 for pushing is pressed with respect to the wafer WF located on a front surface portion 122 side in the Y1 direction, only one sheet of the wafer WF located on the outermost side is taken out from the inside of the wafer cassette WC along the Y1 direction.

As illustrated in FIG. 5A, the wafer WF that can be used as a cutting member is constituted by a copper metal plate (a thickness: approximately 0.3 mm, a width: approximately 34 mm, and a height: approximately 13 mm) that can be heated by the wafer heating heater 110 (refer to FIG. 4) and is formed in a substantially rectangular shape. Furthermore, the wafer WF has two contact points 131 which are connected to the wafer heating heater 110 when being heated.

Figure 7:
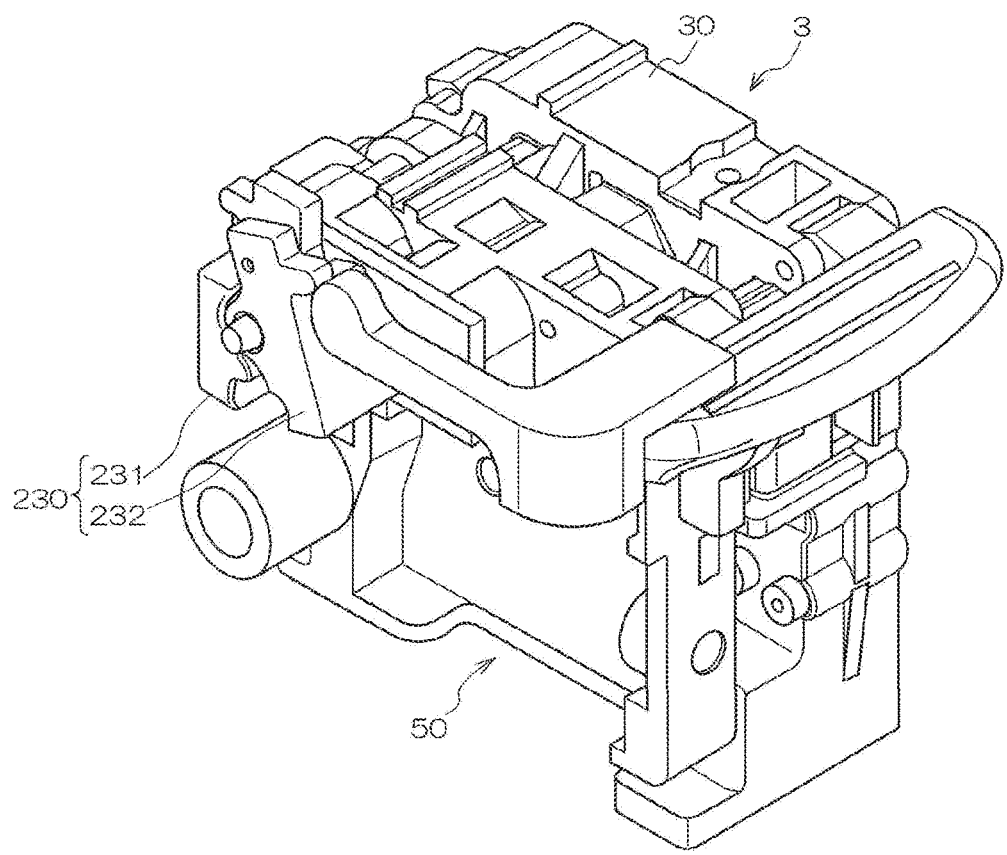
FIG. 7 is a perspective view illustrating main portions of the tube joining device in a state in which the clamp cover section is closed.

Next, description will be given of tube holding portions which respectively hold the tubes T1 and T2 in the tube joining device 1. FIG. 6 and FIG. 7 are perspective views illustrating a state in which the clamp cover section 3 is opened or closed.

As illustrated in FIG. 6, the housing-side clamp unit 50 of the housing 2 includes a first accommodation member 150 and a second accommodation member 160. The first accommodation member 150 and the second accommodation member 160 are disposed with a predetermined gap in a disposition direction (extension direction) of the first tube T1. The first accommodation member 150 includes a substantially U-shaped groove 151a and a protrusion 155 that protrudes to an upward side. The second accommodation member 160 includes a notched portion 161a that is formed to face an outer side surface, a first tube holding portion 163 that fixes and holds the first tube T1, and a protrusion 165 that protrudes to an upward side.

The first tube T1 is disposed in such a manner that a part thereof is suspended in the groove 151a of the first accommodation member 150, and a predetermined portion that is close to the portion that is suspended in the groove 151a is held by the first tube holding portion 163. For example, the first tube holding portion 163 may be formed by an insertion type groove or the like that is formed in conformity to an outer diameter of the first tube T1, but a structure thereof is not particularly limited as long as the first tube T1 can be held in a position-fixed manner. The first tube T1 is held by the housing-side clamp unit 50 in a state of being supported in the groove 151a and of being fixed by the first tube holding portion 163. One end side of the first tube T1 is led out to the outside of the second accommodation member 160 through the notched portion 161a of the second accommodation member 160.

Setting of the first tube T1 to the housing-side clamp unit 50 can be performed, for example, by simple work of setting the clamp cover section 3 to an opened state as illustrated in FIG. 6, and of pushing the first tube T1 from upper sides of the first accommodation member 150 and the second accommodation member 160. Furthermore, the gap 57 formed between the first accommodation member 150 and the second accommodation member 160 is a portion through which the wafer WF is guided when fusing the tubes T1 and T2.

As in the housing-side clamp unit 50, a structure for holding a tube is provided at the inside of the clamp plate 30 provided in the clamp cover section 3. As illustrated in FIG. 6, the clamp plate 30 includes a second tube holding portion 230 that fixes and holds the second tube T2, and a first accommodation member 250, a second accommodation member 260, and a third accommodation member 270 which are disposed with a predetermined interval from the second tube holding portion 230 in a disposition direction (extension direction) of the second tube T2.

The second tube holding portion 230 includes a first clamp member 231 and a second clamp member 232 which grip (pinch) the second tube T2. A biasing force is applied to the clamp members 231 and 232 in a direction of closing a gap between the members in a state in which a force from the outside does not act. According to this, when causing the second tube T2 to be held in the second tube holding portion 230, a user grips a base portion 234 of the clamp members 231 and 232 and enlarges a distance between tip end sides of the clamp members 231 and 232. In addition, the user performs an operation of releasing the gripping of the base portion 234 after disposing the second tube T2 between the clamp members 231 and 232. Furthermore, for example, a structure of applying a biasing force to the clamp members 231 and 232 may be constituted by a known elastic member such as a spring, and the like.

In a tip end portion 235 of the clamp members 231 and 232, a concave portion that forms a groove that covers a part of the outer periphery of the second tube T2 is provided between the clamp members 231 and 232 when closing the clamp members 231 and 232. The groove that is formed when the clamp members 231 and 232 are closed can realize more stable holding of the second tube T2.

The first accommodation member 250 includes a substantially U-shaped groove 251a. Similarly, the second accommodation member 260 also includes a substantially U-shaped groove 261a. The grooves 251a and 261a are provided to suspend and hold the second tube T2 when disposing the second tube T2 in the clamp cover section 3.

The third accommodation member 270 includes a substantially U-shaped groove 271a, a first concave portion 275 and a second concave portion 276 which are inwardly recessed in a concave portion. As in the grooves which are provided in the other accommodation members 250 and 260, the groove 271a is provided to suspend and hold the second tube T2. The first concave portion 275 is a portion that accommodates the protrusion 155 of the first accommodation member 150 of the housing-side clamp unit 50. In addition, the second concave portion 276 is a portion that accommodates the protrusion 165 of the second accommodation member 160 of the housing-side clamp unit 50. When the clamp plate 30 is closed along a direction indicated by an arrow RS in FIG. 6, the first concave portion 275 faces the first protrusion 155, and the first protrusion 155 is inserted into the first concave portion 275. In addition, the second concave portion 276 faces the second protrusion 165, and the second protrusion 165 is inserted into the second concave portion 276. According to this, the third accommodation member 270 of the clamp plate 30 and the second accommodation member 160 of the housing-side clamp unit 50 are integrated with each other. The third accommodation member 270 and the second accommodation member 160 which are integrated with each other form the movable clamp unit 71 that replaces ends of the tubes T1 and T2 which are fused by the wafer WF.

As is simply illustrated in a broken line portion in FIG. 6, for example, a predetermined gear 55 can be formed at the periphery of the third accommodation member 270 of the clamp plate 30 and the periphery of the second accommodation member 160 of the housing-side clamp unit 50. In addition, the gear 55 can be configured to engage with a gear 56G of the clamp motor 56 that drives an operation of replacing positions of ends of the tubes T1 and T2 after fusing the tubes T1 and T2.

Figure 16C:
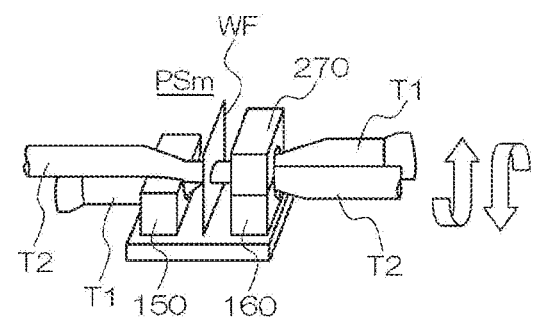

For example, when the clamp motor 56 operates by a command of the control unit 100 (refer to FIG. 4) and rotates the gear 56G, the third accommodation member 270 of the clamp plate 30 and the second accommodation member 160 of the housing-side clamp unit 50 positively rotate by 180° or reversely rotate by 180° in an integrated state. In addition, as illustrated in FIG. 16C, during the rotation, one end side (the right side in the drawing) of the first tube T1 and the second tube T2 which are fused rotates, and the other end side is pressed by the first accommodation member 250 of the clamp plate 30 and the first accommodation member 150 of the housing-side clamp unit 50 and is held therebetween. As a result, a position of the end of the first tube T1 and a position of the end of the second tube T2 after fusing are vertically reversed by 180°. According to this, before the fusing, one end of the second tube T2 is located on an upper side and one end of the first tube T1 is located on a lower side, but after the fusing, the one end of the first tube T1 is located on the upper side, and the one end of the second tube T2 is located on the lower side.

For example, setting of the second tube T2 to the clamp plate 30 can be carried out through simple work only by setting the clamp cover section 3 to an opened state as illustrated in FIG. 6, by operating the second tube holding portion 230 to grip the second tube T2, and by pushing the second tube T2 from downward sides of the accommodation members 250, 260, and 270.

When causing the clamp plate 30 to approach the housing-side clamp unit 50 along the arrow RS, the second tube holding portion 230 provided in the clamp plate 30 relatively approaches the first tube holding portion 163 provided in the housing-side clamp unit 50 in accordance with the approaching movement. In addition, at this time, the second tube T2 that is held by the second tube holding portion 230 is superimposed on the first tube T1 that is held by the first tube holding portion 163, and the tubes T1 and T2 are disposed in a close contact state. As described above, before carrying out the fusing-joining work, it is not necessary for the user to manually superimpose the tubes T1 and T2 on each other, and it is possible to terminate preparation by a simple operation of closing the clamp plate 30 in a state in which the tubes T1 and T2 are respectively held by the holding portions 163 and 230. When the clamp plate 30 is closed as illustrated in FIG. 7, the inside of the clamp plate 30 and the inside of the housing-side clamp unit 50 are isolated from the outside. Accordingly, it is possible to perform fusing and joining of the tubes T1 and T2 disposed between the clamp plate 30 and the housing-side clamp unit 50 in an aseptic condition.

Furthermore, with regard to a shape and a size of the grooves which are formed in the respective portions of the clamp cover section 3 and the housing-side clamp unit 50, the shape and the like are not particularly limited as long as the tubes T1 and T2 can be held. In addition, for example, an inclined guide surface and the like can be formed at the periphery of the grooves to easily perform setting of the tubes T1 and T2 in the grooves.

Next, description will be given of the delivery mechanism 500 of a heating plate member for delivering the wafer WF that is the heating plate member inside the wafer cassette WC to the stand-by position PS3 with reference to FIG. 8 to FIG. 14.

Figure 8:
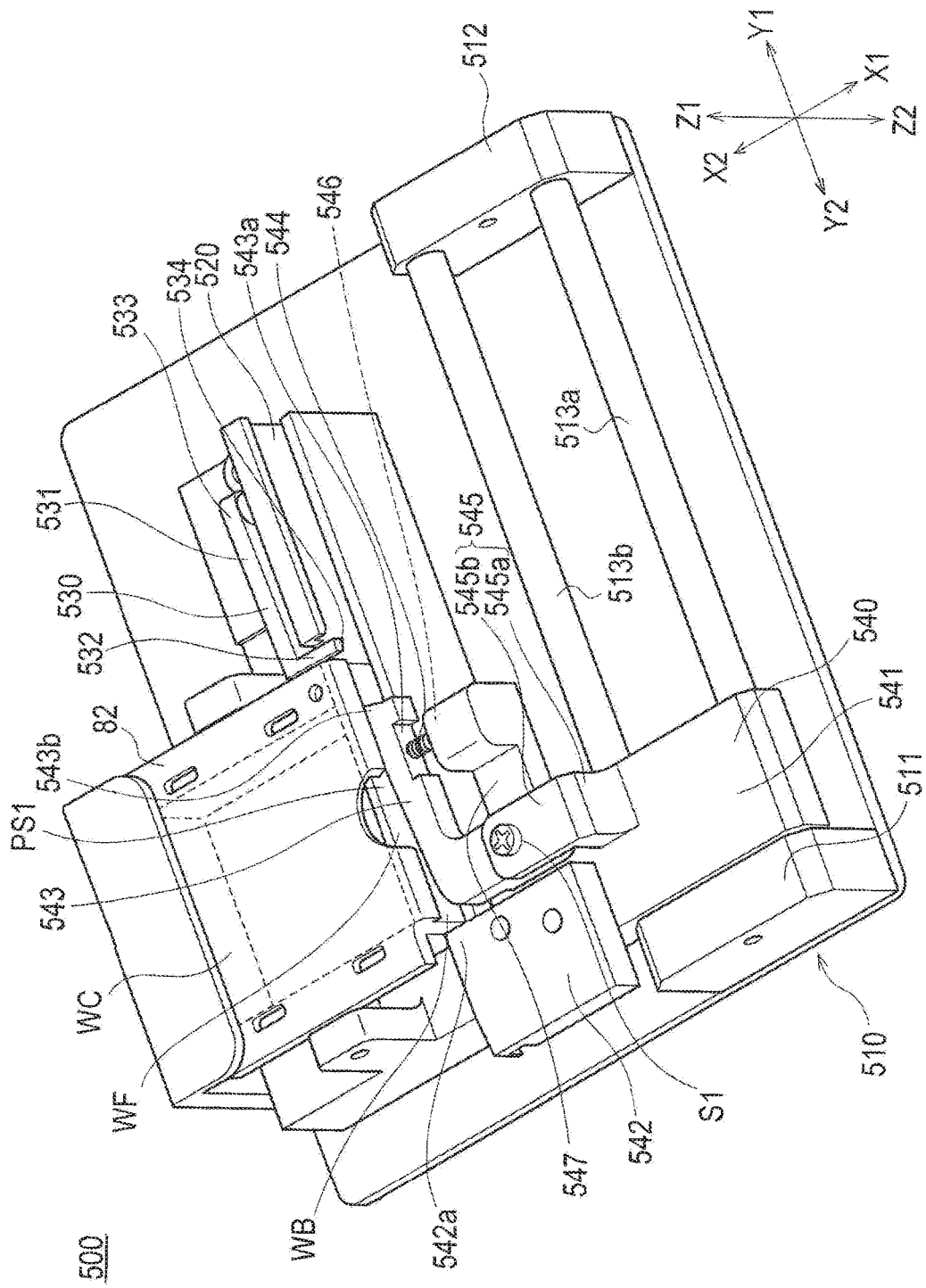
FIG. 8 is a perspective view illustrating a delivery mechanism in a state in which a wafer in the wafer cassette is located at a take-out position.
Figure 9:
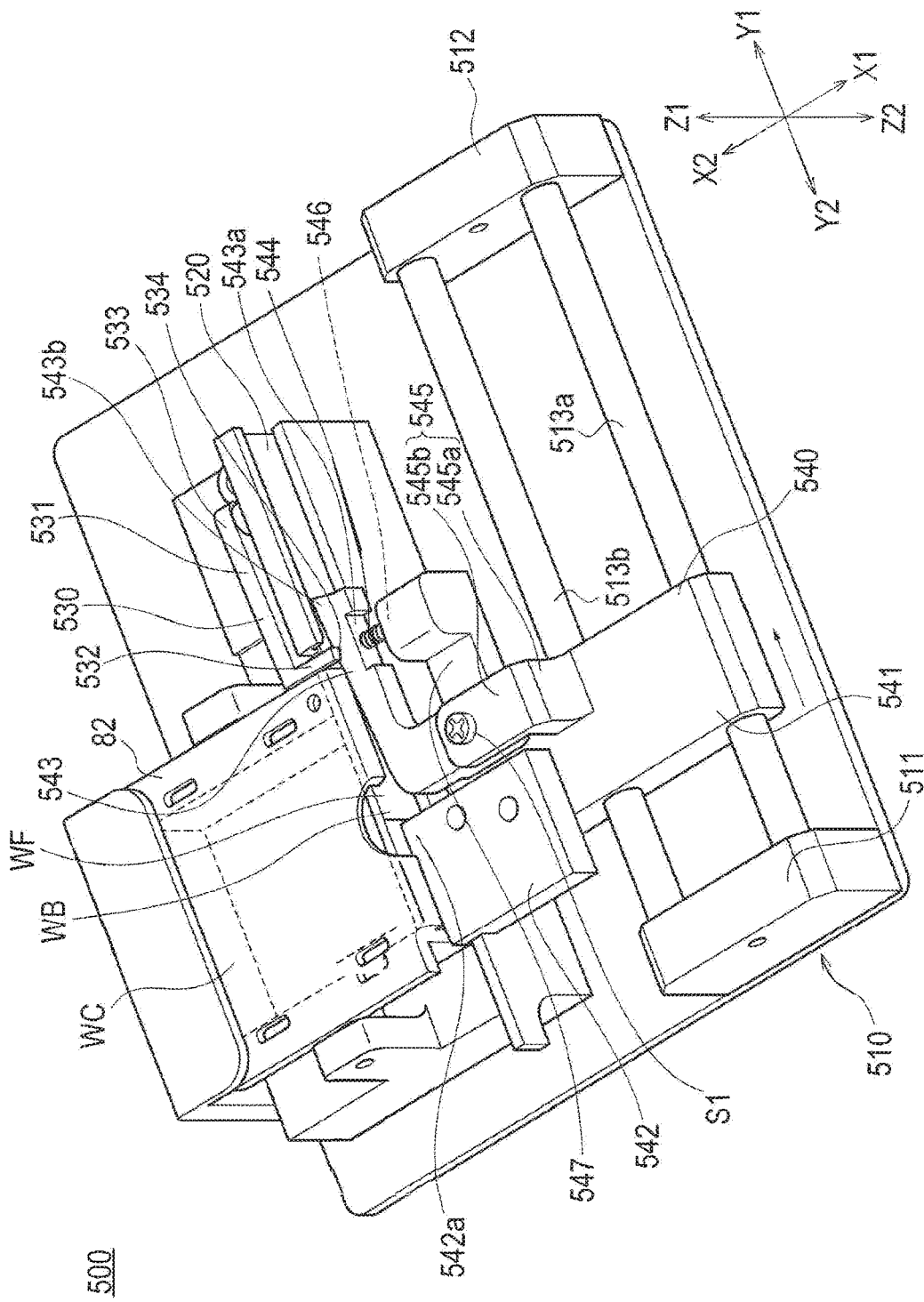
FIG. 9 is a perspective view illustrating a state in which a first pusher member moves the wafer in a Y1 direction in accordance with movement of a moving body in the Y1 direction.
Figure 10:
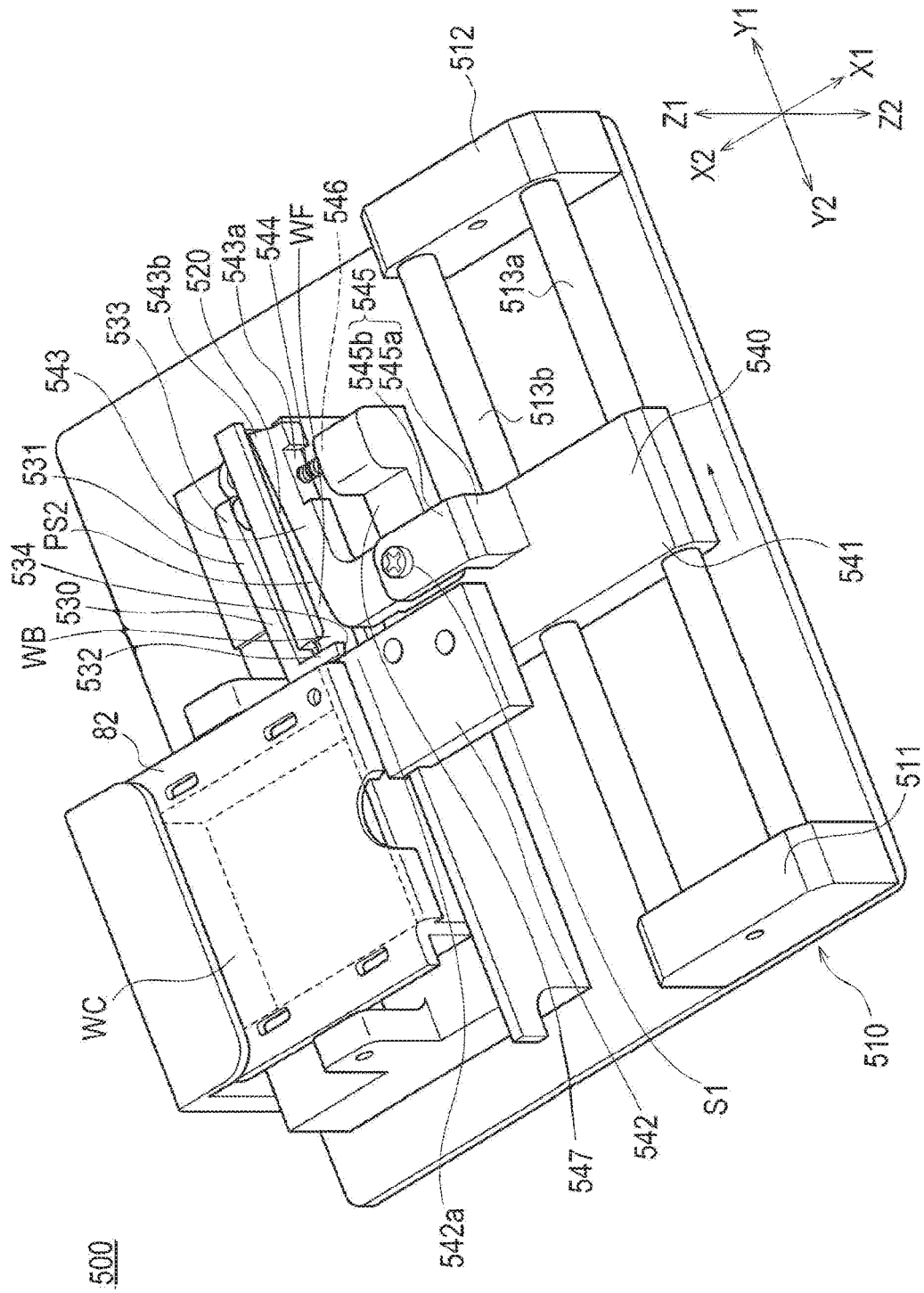
FIG. 10 is a perspective view illustrating a state in which the first pusher member moves the wafer to a first position.
Figure 11:
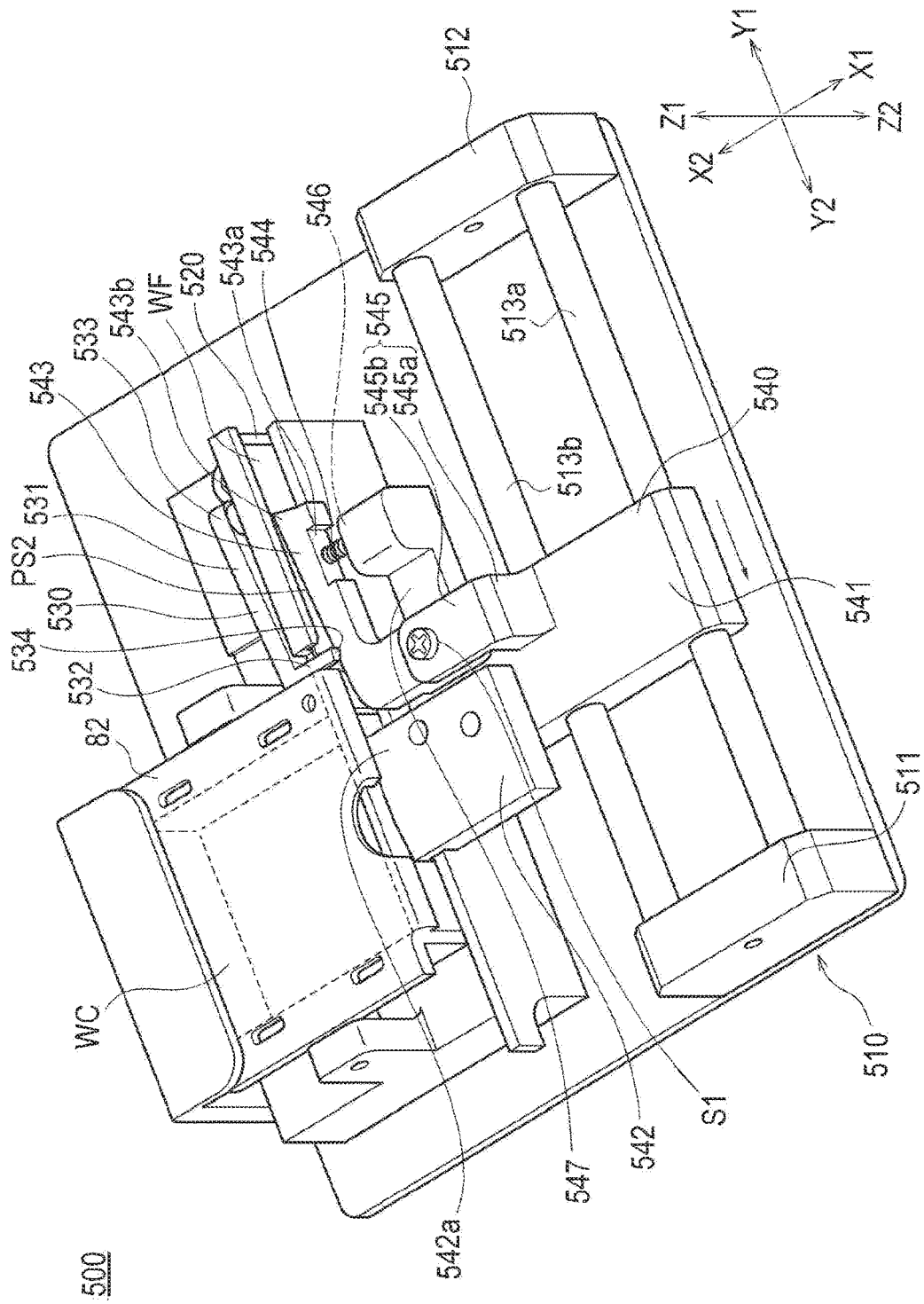
FIG. 11 is a perspective view illustrating a state in which the moving body moves in a Y2 direction.
Figure 12:
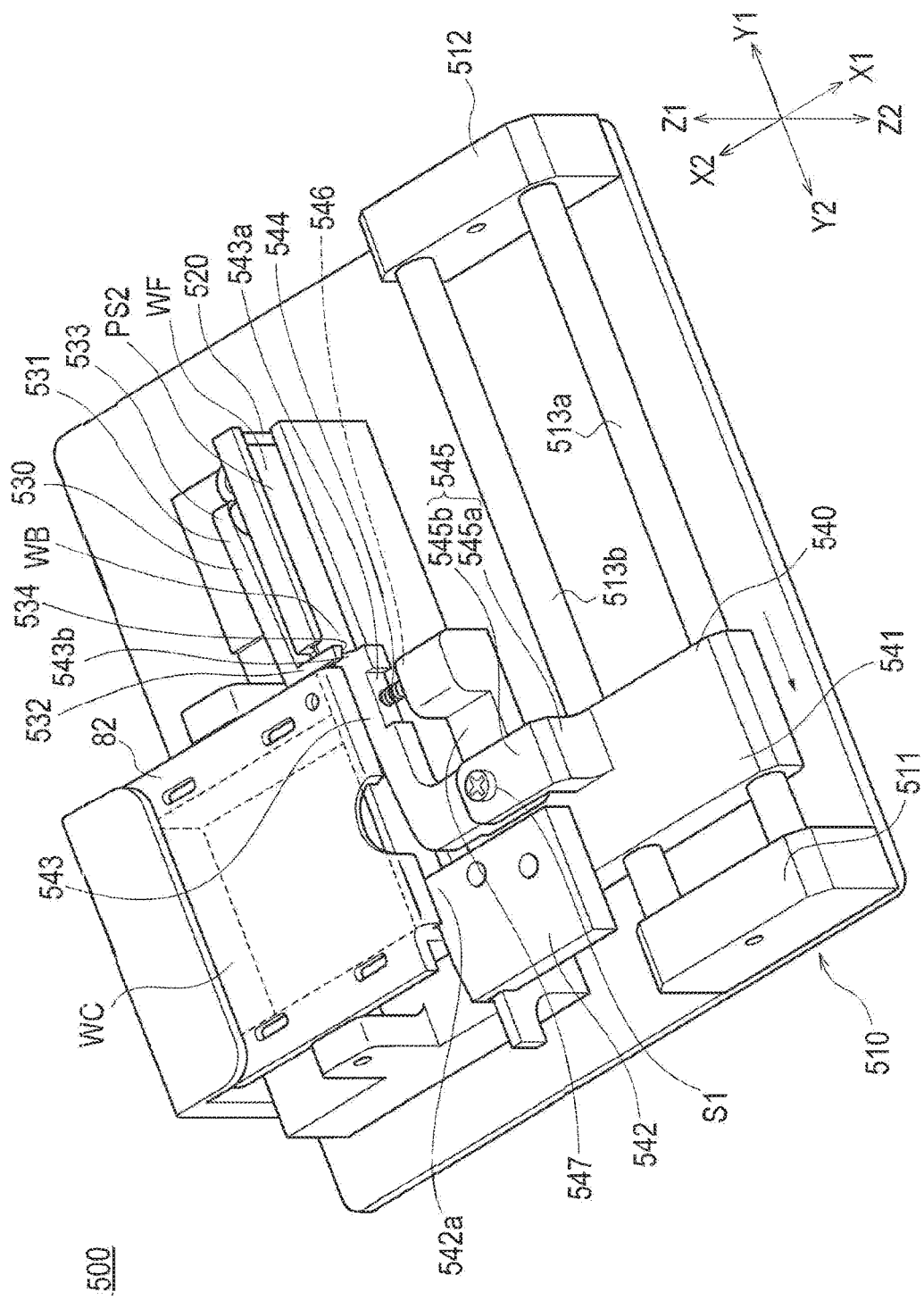
FIG. 12 is a perspective view illustrating a state before movement of the wafer in the Y1 direction by a second pusher member is initiated.
Figure 13:
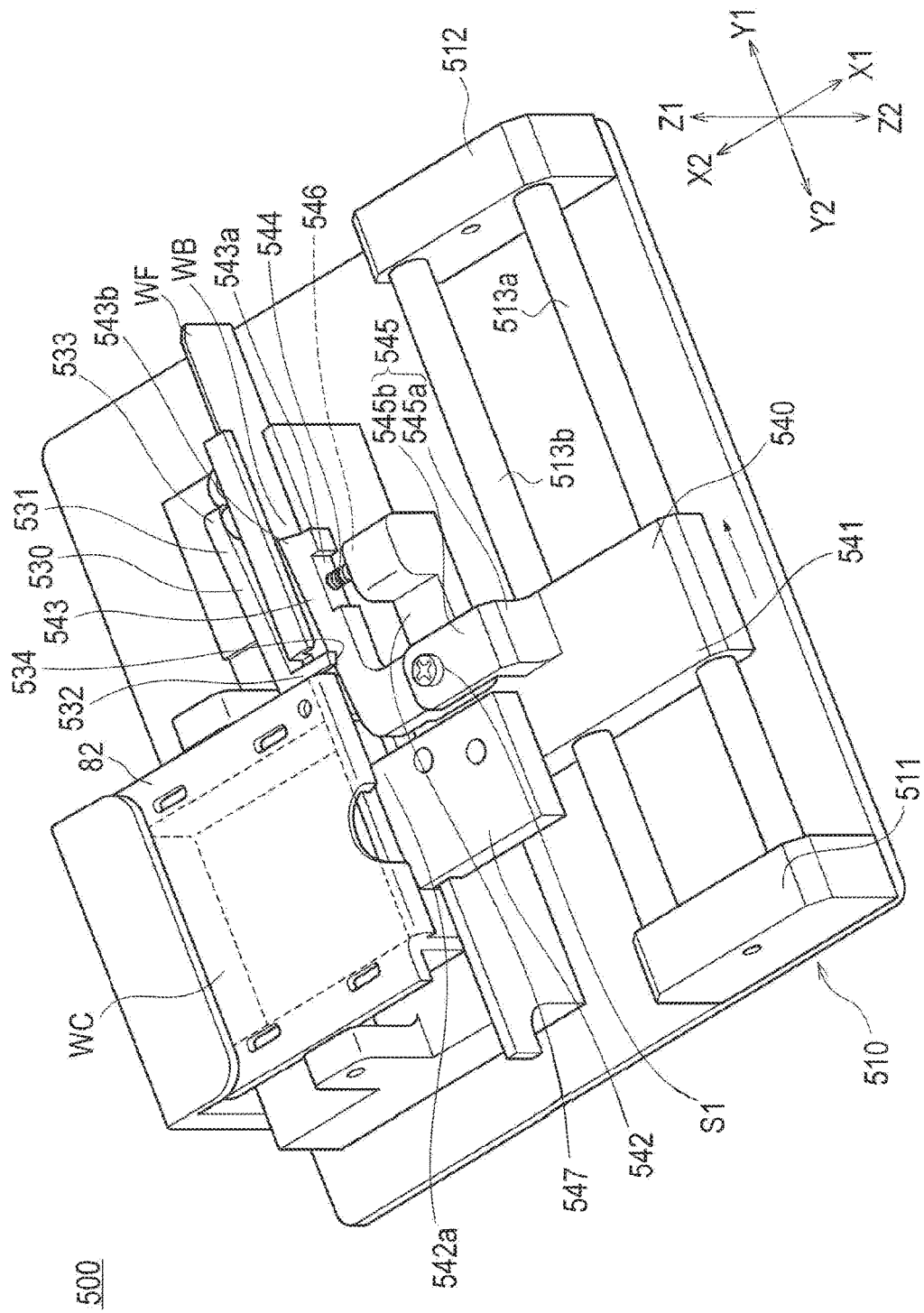
FIG. 13 is a perspective view illustrating a state in which the second pusher member moves the wafer in the Y1 direction in accordance with movement of the moving body in the Y1 direction.
Figure 14:
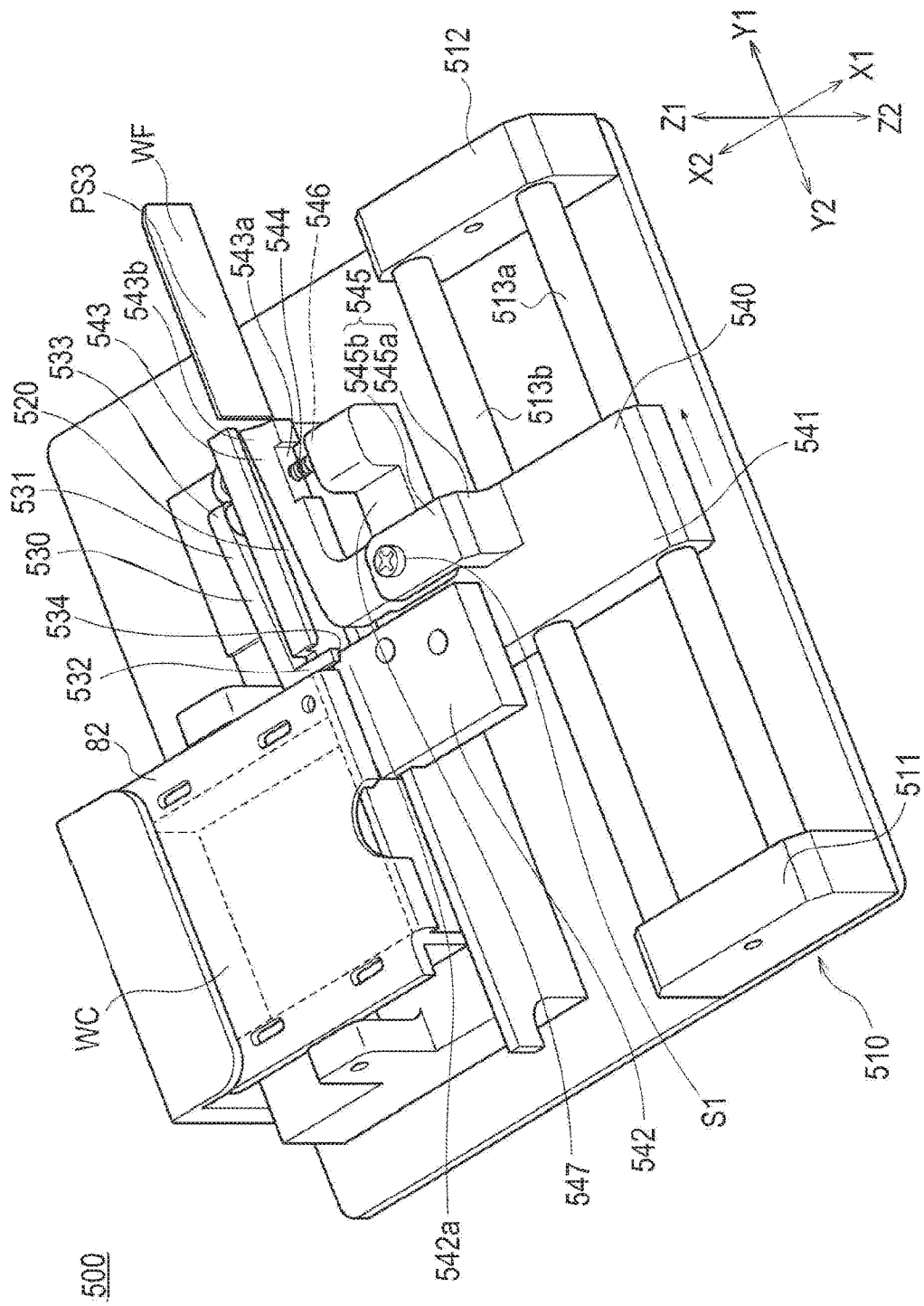
FIG. 14 is a perspective view illustrating a state in which the second pusher member moves the wafer to a stand-by position.

FIG. 8 is a perspective view illustrating the delivery mechanism 500 in a state in which the wafer WF inside the wafer cassette WC is located at a take-out position PS1. FIG. 9 is a perspective view illustrating a state in which a first pusher member 542 moves the wafer WF in the Y1 direction in accordance with movement of the moving body 540 in the Y1 direction. FIG. 10 is a perspective view illustrating a state in which the first pusher member 542 moves the wafer WF to a first position PS2. FIG. 11 is a perspective view illustrating a state in which the moving body 540 is moved in the Y2 direction. FIG. 12 is a perspective view illustrating a state before movement of the wafer WF in the Y1 direction by a second pusher member 543 is initiated. FIG. 13 is a perspective view illustrating a state in which the second pusher member 543 moves the wafer WF in the Y1 direction in accordance with movement of the moving body 540 in the Y1 direction. FIG. 14 is a perspective view illustrating a state in which the second pusher member 543 moves the wafer WF to a stand-by position PS3.

The delivery mechanism 500 is a device that pushes out a front end wafer WF located at the take-out position PS1 illustrated in FIG. 8 inside the wafer cassette WC sheet by sheet in the Y1 direction, and delivers the wafer WF to the stand-by position PS3 of the wafer WF illustrated in FIG. 14.

As illustrated in FIG. 8 to FIG. 14, the delivery mechanism 500 includes a movement operating portion 510 that operates movement of the wafer WF, a guide portion 520 that guides a delivery direction of the wafer WF, and a stopper 530 that is rotatably attached to the guide portion 520.

The movement operating portion 510 includes the moving body 540, a first base portion 511, a second base portion 512, a delivery screw 513a, a guide bar 513b, a motor 103, and a motor drive 104 (refer to FIG. 4).

The moving body 540 includes a main body portion 541 that can slide in the Y1 direction along the delivery screw 513a and the guide bar 513b, a first pusher member 542 that is attached to a Z1 direction side or an X2 direction side of the main body portion 541, a second pusher member 543 that is formed in the main body portion 541 to be adjacent to a Y1 direction side of the first pusher member 542, and a biasing member 544 that applies a predetermined biasing force to the second pusher member 543.

The main body portion 541 includes a pinching portion 545 that pinches the second pusher member 543, and a first sitting portion (the surface of the contacting the spring) 546 in which the biasing member 544 sits.

The pinching portion 545 includes a vertical wall portion 545a that extends from the main body portion 541 in the Z1 direction, and an extended portion 545b that extends from the vertical wall portion 545a in the X2 direction.

The first sitting portion 546 is formed at a position that is spaced away from the main body portion 541 by a predetermined distance in the Y1 direction. The first sitting portion 546 is connected to the main body portion 541 through a connection portion 547.

The first pusher member 542 is provided to perform forward movement and backward movement along a delivery direction (Y1 direction). The first pusher member 542 is attached to an upward side of the main body portion 541. Means for attaching the first pusher member 542 to the main body portion 541 is not particularly limited, and is fixing with a screw as an example. A pressing portion (corresponding to a tip end of the first pusher member) 542a that presses the wafer WF inside the wafer cassette WC is formed in the first pusher member 542 at a corner in the X2 direction and the Y1 direction. When the first pusher member 542 moves in the Y1 direction in accordance with movement of the main body portion 541 in the Y1 direction, the pressing portion 542a can linearly deliver only one sheet of the front end wafer WF inside the cassette WC stored in the wafer cassette storage unit 82 along the Y1 direction. At this time, the first pusher member 542 delivers the wafer WF to a first position PS2 located between the take-out position PS1 at which the wafer WF is taken out from the wafer cassette WC and the stand-by position PS3 (refer to FIG. 8 to FIG. 10).

The second pusher member 543 is provided to perform forward movement and backward movement along the deliver direction (Y1 direction) in combination with the first pusher member 542. After the wafer WF is delivered to the first position PS2 by the first pusher member 542, the second pusher member 543 moves in the Y2 direction in combination with the first pusher member 542 (refer to FIG. 11). In addition, the second pusher member 543 initiates a delivery operation of delivering the wafer WF to the stand-by position PS3 (refer to FIG. 12).

The second pusher member 543 is pinched in the pinching portion 545, and is attached to freely rotate around an axis of a screw portion S1. The second pusher member 543 is formed in an L shape when viewed from an upward side. In the second pusher member 543, a second sitting portion 543a in which the biasing member 544 sits is formed at a portion on a side opposite to the side in which the screw portion S1 is formed.

A force for rotation in a counter-clockwise direction is applied to the second sitting portion 543a by the biasing member 544 when viewed from an upward side. In the second pusher member 543, a pressing portion (corresponding to a tip end of the second pusher member) 543b that presses the wafer WF is formed in a corner in the X2 direction and the Y1 direction. According to this, when the second pusher member 543 moves in the Y1 direction in accordance with movement of the main body portion 541 in the Y1 direction, the pressing portion 543b can linearly deliver the wafer WF in the Y1 direction. At this time, the second pusher member 543 delivers the wafer WF from the first position PS2 to the stand-by position PS3 (refer to FIG. 12 to FIG. 14).

While the wafer WF is moved by the first pusher member 542 from the take-out position PS1 to the first position PS2, a lateral surface of the second pusher member 543 comes into contact with the wafer WF to assist movement of the wafer WF between the second pusher member 543 and the guide portion 520.

The biasing member 544 applies a biasing force for causing the lateral surface of the second pusher member 543 to come into contact with the wafer WF until the wafer WF reaches the first position PS2 (refer to FIG. 8 to FIG. 10).

When initiating movement of the wafer WF by the second pusher member 543 (refer to FIG. 12), the biasing member 544 applies a biasing force toward the X2 direction so that a position of the pressing portion 543b of the second pusher member 543 matches a position of a base end WB of the wafer WF.

The first base portion 511 and the second base portion 512 face each other with an interval, and are provided to erect in the Z1 direction in a bottom chassis 2N of the housing 2.

One end of the delivery (feed) screw 513a is rotatably attached to the first base portion 511, and the other end of the delivery screw 513a is rotatably attached to the second base portion 512. The delivery screw 513a is positively rotated or reversely rotated by the control unit 100 to move the moving body 540 in the Y1 direction or the Y2 direction.

The guide bar 513b is a thin member that has a circular cross-section and is fixed between the first base portion 511 and the second base portion 512. The moving body 540 moves in the Y1 or Y2 direction along the delivery screw 513a and the guide bar 513b. A position of the moving body 540 in the Y1 or Y2 direction can be detected by the forward edge sensor 105, the intermediate sensor 106, and the backward edge sensor 107 (refer to FIG. 4).

As illustrated in FIG. 8 to FIG. 14, the guide portion 520 is disposed on an extension line of the wafer cassette WC along the Y1 direction. The guide portion 520 guides the wafer WF in the Y1 direction while supporting a lower end surface of the wafer WF that is pushed out from the wafer cassette WC in the Y1 direction. According to this, the guide portion 520 includes a groove having a U-shaped cross-section, and a groove width thereof is slightly greater than the thickness (approximately 0.3 mm) of the wafer WF.

The stopper 530 is formed in an L-shape when viewed from an upward side, and includes a first extended portion 531 that extends in the Y1 direction, and a second extended portion 532 that extends in an X1 direction. The first extended portion 531 is attached to the guide portion 520 to rotate around an axis in the X1 direction at an end 533.

A tapered portion 534, which is inclined in a Z2 direction along the Y1 direction when viewed from the X1 direction, is formed in the second extended portion 532. In a normal state, in the stopper 530, the tapered portion 534 is in contact with the guide portion 520 due to own weight.

Since the stopper 530 is provided as described above, when the wafer WF moves in the Y1 direction, the tapered portion 534 of the stopper 530 is moved in the Z1 direction as the wafer WF moves in the Y1 direction. According to this, the wafer WF can move in the Y1 direction. On the other hand, when the wafer WF moves in the Y2 direction, the wafer WF comes into contact with a right end of the tapered portion 534, and thus movement is regulated.

When receiving a command from the control unit 100, the motor drive 104 drives the motor 103 to move the wafer inside the wafer cassette WC to the stand-by position PS3.

According to the delivery mechanism 500 configured as described above, it is possible to switch an operation of delivering the wafer WF by the first pusher member 542 to an operation of delivering the wafer WF by the second pusher member 543 in synchronization with forward movement and backward movement of the first pusher member 542 and the second pusher member 543.

According to this, in comparison to the case of using a pusher member corresponding to a total length of a movement distance of the first pusher member 542 and a movement distance of the second pusher member 543, it is possible to further shorten a retraction distance of the first pusher member 542 in the Y2 direction in relation to the wafer WF inside the wafer cassette WC. Accordingly, it is possible to shorten a movement distance of the delivery mechanism 500 when delivering the wafer WF from the take-out position PS1 to the stand-by position PS3.

Next, a work process of joining the tubes T1 and T2 will be described with reference to FIG. 8 to FIGS. 16A to 16D and other drawings. FIG. 15 and FIGS. 16A to 16D are views schematically illustrating a fusing-joining work flow by the tube joining device 1.

First, a user lifts up the clamp cover section 3 of the tube joining device 1 in an arrow RT direction illustrated in FIG. 6. In this case, the clamp cover section 3 is separated from the housing-side clamp unit 50 and the housing-side clamp unit 50 enters a state of being opened to the outside as illustrated in FIG. 6.

Next, as illustrated in FIG. 16A, the user sets the second tube T2 in the second tube holding portion 230, and sets the first tube T1 in the first tube holding portion 163 of the housing-side clamp unit 50. Furthermore, a procedure of setting the tubes T1 and T2 may be set to an opposite procedure.

Next, as illustrated in FIG. 7 and FIG. 16B, the user causes the clamp cover section 3 to approach the housing-side clamp unit 50, and closes the clamp cover section 3. In addition, through the work, the second tube T2 that is held by the second tube holding portion 230 is superimposed on the first tube T1 that is held by the first tube holding portion 163. As described above, holding of the second tube T2 by the second tube holding portion 230 is released when the clamp plate 30 is closed.

The user pushes the joining button 7E of the operation panel unit 7 after closing the clamp plate 30 (refer to FIG. 2A). Then, the fusing work by the wafer WF is initiated.

When the fusing work is initiated, as illustrated in FIG. 16B, the wafer WF is moved by the delivery mechanism 500 from the wafer cassette WC to the stand-by position PS3 that is located on a downward side of the tubes T1 and T2. At this time, the wafer WF is heated to, for example, approximately 300° C. through heating by the wafer heating heater 110. As illustrated in FIG. 16B, the heated wafer WF ascends from the stand-by position PS3 indicated by a broken line to the fusing position PSm indicated by a solid line in accordance with an operation of the cam motor 117. As a result, the tubes T1 and T2 are fused by the wafer WF. Hereinafter, a use method of the delivery mechanism 500 will be described in detail.

The wafer cassette WC is stored in the wafer cassette storage unit 82 in advance. The moving body 540 of the delivery mechanism 500 is positioned at a position (base end in the Y2 direction) illustrated in FIG. 8.

At this time, the pressing portion 542a of the first pusher member 542 collides with the base end WB of the front end wafer WF inside the wafer cassette WC. In addition, when the moving body 540 is linearly moved in the Y1 direction along the guide bar 513b, the first pusher member 542 moves the wafer WF from the take-out position PS1 in the Y1 direction (refer to FIG. 9). In addition, as illustrated in FIG. 10, the moving body 540 is moved in the Y1 direction up to a position (corresponding to the first position PS2) at which the base end WB of the wafer WF passes over the tapered portion 534 of the stopper 530.

Next, the operation of delivering the wafer WF by the first pusher member 542 is switched to the operation of delivering the wafer WF by the second pusher member 543. Hereinafter, the switching will be described in detail. First, as illustrated in FIG. 11, the moving body 540 is moved in the Y2 direction. At this time, the wafer WF receives a force of movement in the Y2 direction due to a frictional force of the second pusher member 543 that receives a force in the X2 direction by the biasing member 544, but the wafer WF comes into contact with the right end of the stopper 530 and thus movement in the Y2 direction is regulated. That is, while the position of the wafer WF is fixed to the first position PS2, the moving body 540 moves backward in the Y2 direction. In addition, as illustrated in FIG. 12, the pressing portion 543b of the second pusher member 543 moves the moving body 540 in the Y2 direction until the pressing portion 543b passes over the base end WB of the wafer WF. When the moving body 540 moves in the Y2 direction until the pressing portion 543b of the second pusher member 543 passes over the base end WB of the wafer WF, a position of the pressing portion 543b of the second pusher member 543 matches the position of the base end WB of the wafer WF due to the biasing force of the biasing member 544.

Next, as illustrated in FIG. 13, the moving body 540 is linearly moved in the Y1 direction, and thus the second pusher member 543 of the moving body 540 moves the wafer WF in the Y1 direction. In addition, as illustrated in FIG. 14, the moving body 540 is moved in the Y1 direction up to a position (corresponding to the stand-by position PS3) at which the base end WB of the wafer WF passes over the guide portion 520. According to the above-described method, the delivery mechanism 500 delivers the wafer WF from the take-out position PS1 to the stand-by position PS3.

Next, as illustrated in FIG. 16C, the clamp motor 56 rotates the gear 56G (refer to FIG. 6). The third accommodation member 270 of the clamp plate 30 and the second accommodation member 160 of the housing-side clamp unit 50 rotate by 180° while holding the first tube T1 and the second tube T2, respectively. As a result, the fused end of the first tube T1 is disposed on an upper side, and the fused end of the second tube T2 is disposed on a lower side.

Figure 16D:
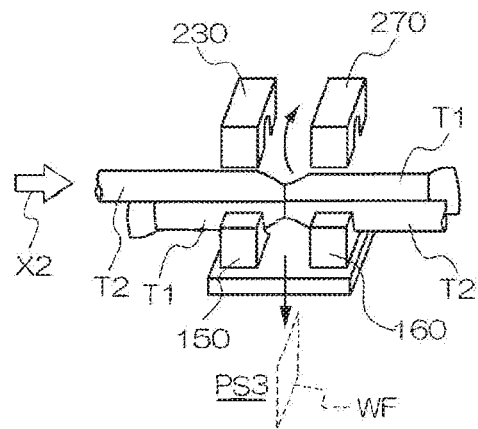

Next, as illustrated in FIG. 16D, the wafer WF descends from the fusing position PSm to the stand-by position PS3, and the tubes T1 and T2 which are positioned on a non-rotation side are pushed to the X2 direction. According to this, an end of the first tube T1 that is located on one side rotated by 180° is pressed and joined to an end of the second tube T2 on the other side that is not rotated. In addition, an end of the second tube T2 that is located on the one side rotated by 180° is pressed and joined to an end of the first tube T1 that is located on the other side that is not rotated. Then, the tubes T1 and T2 are cooled down, and thus joining is completed.

After the joining is completed, the wafer WF that has been used in the fusing is discharged to the take-out port 58. The user can take out the wafer WF that has been used from the take-out port 58 by pinching the wafer WF with fingers.

Figure 17A:
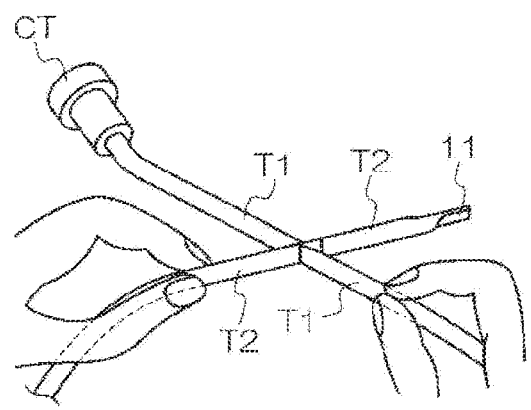
Figure 17B:
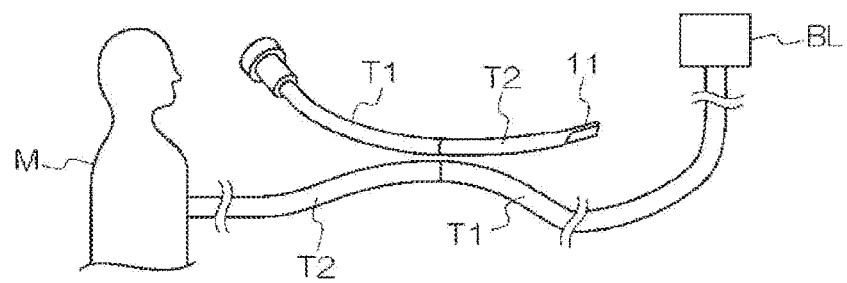

Then, the user lifts up the clamp cover section 3 in the arrow RT direction illustrated in FIG. 6. In this manner, the clamp cover section 3 is detached from the housing-side clamp unit 50 as illustrated in FIG. 6. As illustrated in FIGS. 17A and 17B, the user detaches and separates the tubes T1 and T2 after joining from the housing-side clamp unit 50. As described above, it is possible to conveniently join the tube T1 on the dialysis fluid bag BL side and the tube T2 on a user M side as illustrated in FIG. 15 in an aseptic condition. Furthermore, it is also possible to construct the tube joining device 1 in such a manner that separation of the tubes T1 and T2 which remain in the housing-side clamp unit 50 after joining is performed, for example, in synchronization with the operation of lifting up the clamp cover section 3.

As described above, the tube joining device 1 according to this embodiment is a tube joining device 1 that fuses an end of the first tube T1 and an end of the second tube T2 by a plate-shaped wafer WF that is heated, and replaces the fused end of the first tube T1 and the fused end of the second tube T2 and joins the fused ends in an aseptic condition. The tube joining device 1 includes the housing 2 in which the first tube T1 and the second tube T2 are set, the wafer cassette storage unit 82 to which the cassette WC storing the wafer WF is detachably mounted, the control unit 100 that performs operation control, and the delivery mechanism 500 that delivers the wafer WF accommodated in the cassette WC to the stand-by position PS3, at which the wafer WF stands by, by a command of the control unit 100 when fusing the first tube T1 and the second tube T2. The delivery mechanism 500 includes the first pusher member 542 that is provided to perform forward movement and backward movement along the delivery direction (Y1 direction) and delivers the wafer WF to the first position PS2 that is set between the take-out position PS1 at which the wafer WF is taken out from the cassette WC and the stand-by position PS3, and the second pusher member 543 that is provided to perform forward movement and backward movement along the delivery direction in combination with the first pusher member 542, and delivers the wafer WF from the first position PS2 to the stand-by position PS3. It is possible to switch an operation of delivering the wafer WF by the first pusher member 542 to an operation of delivering the wafer WF by the second pusher member 543 in synchronization with forward movement and backward movement of the first pusher member 542 and the second pusher member 543. According to the tube joining device 1 configured as described above, in comparison to the case of using a pusher member corresponding to a total length of a movement distance of the first pusher member 542 and a movement distance of the second pusher member 543, it is possible to further shorten a retraction distance of the first pusher member 542 in the Y2 direction in relation to the wafer WF inside the wafer cassette WC. Accordingly, it is possible to shorten a movement distance of the delivery mechanism 500 when delivering the wafer WF from the take-out position PS1 to the stand-by position PS3. As a result, it is possible to provide a tube joining device in which the degree of freedom of device design is improved.

In addition, the first pusher member 542 is disposed on a backward side of the second pusher member 543 in the delivery direction, and moves forward along the delivery direction from a backward side in comparison to the take-out position PS1 to deliver the wafer WF to the first position PS2. The second pusher member 543 moves to a backward side of the wafer WF in combination with the first pusher member 542 after the wafer WF is delivered to the first position PS2 by the first pusher member 542, and initiates a delivery operation of delivering the wafer WF from the first position PS2 to the stand-by position PS3. According to the tube joining device 1 configured as described above, it is possible to appropriately switch the operation of delivering the wafer WF by the first pusher member 542 and the operation of delivering the wafer WF by the second pusher member 543.

In addition, the tube joining device 1 further includes the guide portion 520 that guides movement of the wafer WF. The first pusher member 542 moves forward in the delivery direction in a state in which the pressing portion 542a comes into contact with the base end WB of the wafer WF to deliver the wafer WF to the first position PS2. The second pusher member 543 assists movement of the wafer WF between the second pusher member 543 and the guide portion 520 in a state in which a lateral surface comes into contact with the wafer WF while the wafer WF is moving to the first position PS2. In addition, the second pusher member 543 moves forward in the delivery direction in a state in which the pressing portion 543b comes into contact with the base end WB of the wafer WF when moving the wafer WF to the stand-by position PS3. According to the tube joining device 1 configured as described above, it is possible to appropriately move the wafer WF to the stand-by position PS3.

In addition, the tube joining device 1 further includes the biasing member 544 that applies a biasing force to the second pusher member 543. The biasing member 544 applies the biasing force so that the lateral surface of the second pusher member 543 comes into contact with the wafer WF until the wafer WF reaches the first position PS2, and applies the biasing force so that a position of the pressing portion 543b of the second pusher member 543 matches a position of the base end WB of the wafer WF when movement of the wafer WF by the second pusher member 543 is initiated. According to the tube joining device 1 configured as described above, it is possible to appropriately move the wafer WF to the first position PS2, and it is possible to appropriately switch the operation of delivering the wafer WF by the first pusher member 542 to the operation of delivering the wafer WF by the second pusher member 543.

In addition, the stopper 530 is provided to prevent the wafer WF from moving in combination with the second pusher member 543 due to the biasing force when the second pusher member 543 moves to a backward side of the wafer WF after the wafer WF is delivered to the first position PS2. According to the tube joining device 1 configured as described above, it is possible to appropriately switch the operation of delivering the wafer WF by the first pusher member 542 and the operation of delivering the wafer WF by the second pusher member 543.

The invention is not limited to the embodiment, and various modifications can be made in a range not departing from the appended claims.

The aseptic joining device of the invention is not limited to aseptic joining between two bold tubes for exchanging the peritoneal dialysis fluid. For example, the aseptic joining device of the invention can be used to automatically join two vinyl chloride tubes which have the same diameter and are used in blood transfusion in an aseptic condition. There is no concern of bacterium contamination when joining the two tubes, and it is possible to maintain sterilization of the tube, blood components in the bag, and the like.

In addition, in the embodiment, the transfer operations of the cutting member are switched by two pusher members. However, the number of the pusher members is not limited to two, and may be three or greater.

With regard to the respective configurations of the embodiment, a part of the configurations may be omitted, or may be combined with other configurations in an arbitrarily manner.

Priority is claimed on Japanese Patent Application No. 2017-059278, filed Mar. 24, 2017, the content of which is incorporated herein by reference.

The invention claimed is:

1. A tube joining device that fuses an end of a first tube and an end of a second tube in an aseptic condition, comprising:

a plurality of wafers;
a cassette that stores the plurality of wafers;
means for heating a selected wafer of the plurality of wafers;
a housing in which the first tube and the second tube are set;
a cassette mounting portion to which the cassette that stores the plurality of wafers is detachably mounted;
a control unit for controlling operation of the tube joining device;
a moving body which is configured to move along a guide bar to transport said selected wafer linearly in a delivery direction;
a plurality of sensors in electrical communication with said control unit and configured to detect a position of said moving body along the delivery direction;
a first pusher member coupled to the moving body configured to perform forward movement and backward movement along the delivery direction and to deliver the selected wafer to a first position that is set between a take-out position at which the selected wafer is taken out from the cassette and a stand-by position; and
a second pusher member coupled to the moving body configured to perform forward movement and backward movement along the delivery direction, the second pusher member being connected with the first pusher member such that the first and second pusher members move together during forward and backward movement along the delivery direction, and the second pusher member delivers the selected wafer from the first position to the stand-by position,
wherein an operation of delivering the selected wafer by the first pusher member is capable of being switched to an operation of delivering the selected wafer by the second pusher member in synchronization with forward movement and backward movement of the first pusher member and the second pusher member.

2. The tube joining device according to claim 1,
wherein the first pusher member moves forward along the delivery direction to deliver the selected wafer to the first position, and
the second pusher member moves backward along the delivery direction to move the selected wafer from the first position to the stand-by position.

3. The tube joining device according to claim 2, further comprising:
a guide portion that guides movement of the selected wafer,
wherein the first pusher member comprises a first tip end which comes into contact with a base end of the selected wafer, and
wherein the second pusher member comprises a second tip end and a lateral surface, and
the tube joining device further comprises a biasing member causing the lateral surface of the second pusher member to come into contact with the selected wafer.

4. The tube joining device according to claim 3,
wherein the biasing member applies a biasing force so that the lateral surface of the second pusher member comes into contact with the selected wafer until the selected wafer reaches the first position, and
the biasing member applies the biasing force so that a position of the second tip end matches a position of the base end of the selected wafer when the second pusher member delivers the selected wafer to the stand-by position.

5. The tube joining device according to claim 4, further comprising a stopper which is provided to prevent the selected wafer from being moved by the second pusher member due to the biasing force when the second pusher member moves backward along the delivery direction.

6. The tube joining device according to claim 1, further comprising:
a guide portion that guides movement of the selected wafer,
wherein the first pusher member comprises a first tip end which comes into contact with a base end of the selected wafer to deliver the selected wafer to the first position, and
the second pusher member comprises a second tip end and a lateral surface, and in which the lateral surface of the second pusher member comes into contact with the selected wafer while the selected wafer is delivered to the first position, and moves forward in the delivery direction in a state in which the second tip end comes into contact with the base end of the selected wafer when the selected wafer is delivered to the stand-by position.

7. The tube joining device according to claim 6, further comprising:
a biasing member that applies a biasing force to the second pusher member,
wherein the biasing member applies the biasing force so that the lateral surface of the second pusher member comes into contact with the selected wafer until the selected wafer reaches the first position, and
the biasing member applies the biasing force so that a position of the lateral surface matches a position of the base end of the selected wafer when the second pusher member is moving the selected wafer.

8. The tube joining device according to claim 7, further comprising a stopper which is provided to prevent the selected wafer from being moved by the second pusher member due to the biasing force when the second pusher member moves backward along the delivery direction.

9. The tube joining device according to claim 1,
wherein the second pusher member comprises a second tip end and a lateral surface, and
the tube joining device further comprises:
a biasing member that applies a biasing force to the second pusher member,
wherein the biasing member applies the biasing force so that the lateral surface of the second pusher member comes into contact with the selected wafer until the selected wafer reaches the first position, and
the biasing member applies the biasing force so that a position of the second tip end of the second pusher member matches a position of a base end of the selected wafer when moving the selected wafer.

10. The tube joining device according to claim 9, further comprising a stopper which is provided to prevent the selected wafer from being moved by the second pusher member due to the biasing force when the second pusher member moves backward along the delivery direction.

11. A tube joining device that fuses an end of a first tube and an end of a second tube in an aseptic condition, comprising:
a housing comprising:
a cassette storage area configured to receive a cassette, the cassette comprising a plurality of metal plates stored therein;
a cassette insertion opening disposed in the housing adjacent the cassette storage area, the cassette insertion opening configured to allow detachable mounting of the cassette with the cassette storage area;

a clamp that is configured to hold a portion of the first tube relative to a portion of the second tube inside the housing;

a linear actuator disposed in the housing, the linear actuator comprising:
 a guide bar extending from a first end of the linear actuator to a second end of the linear actuator; and
 a body that is configured to slide in a linear direction along the guide bar;

a first push block attached to the body configured to contact a selected metal plate of the plurality of metal plates when the body is disposed at a point adjacent the first end and when the cassette is detachably mounted with the cassette storage area, and move the selected metal plate from the cassette to a first position set a first distance from the cassette as the body slides a first time to a first point disposed between the first end and the second end; and a second push block attached to the body configured to contact the selected metal plate after the body returns from the first point to the point adjacent the first end and move the selected metal plate from the first position to a second position a second distance from the cassette as the body second slides a second time to the first point disposed between the first end and the second end, wherein the second distance is greater than the first distance.

12. The tube joining device according to claim 11, further comprising:
 a heater disposed inside the housing and configured to heat the selected metal plate of the plurality of metal plates.

13. The tube joining device according to claim 12, further comprising:
 a processor; and
 a memory coupled with and readable by the processor and storing therein a control program that, when executed by the processor, causes the processor to control operations of the tube joining device.

14. The tube joining device according to claim 13, further comprising:
 a plurality of sensors in electrical communication with the processor and configured to detect a position of the body sliding in the linear direction along the guide bar.

15. The tube joining device according to claim 14, wherein each metal plate of the plurality of metal plates are made from copper.

16. The tube joining device according to claim 15, wherein, in the second position, the selected metal plate is disposed adjacent the portion of the first tube and adjacent the portion of the second tube.

17. A method of fusing an end of a first tube and an end of a second tube in an aseptic condition, the method comprising:
 providing a tube joining device comprising:
  a plurality of wafers;
  a cassette that stores the plurality of wafers;
  means for heating a selected wafer of the plurality of wafers;
  a housing in which the first tube and the second tube are set;
  a cassette mounting portion to which the cassette that stores the plurality of wafers is detachably mounted;
  a control unit for controlling operation of the tube joining device;
  a moving body which is configured to move along a guide bar to transport said selected wafer linearly in a delivery direction;
  a plurality of sensors in electrical communication with said control unit and configured to detect a position of said moving body along the delivery direction;
  a first pusher member coupled to the moving body configured to perform forward movement and backward movement along the delivery direction and to deliver the selected wafer to a first position that is set between a take-out position at which the selected wafer is taken out from the cassette and a stand-by position; and
  a second pusher member coupled to the moving body configured to perform forward movement and backward movement along the delivery direction, the second pusher member being connected with the first pusher member such that the first and second pusher members move together during forward and backward movement along the delivery direction, and the second pusher member delivers the selected wafer from the first position to the stand-by position,
  wherein an operation of delivering the selected wafer by the first pusher member is capable of being switched to an operation of delivering the selected wafer by the second pusher member in synchronization with forward movement and backward movement of the first pusher member and the second pusher member;
 heating the selected wafer while the selected wafer is in the stand-by position; and
 moving the selected wafer from the stand-by position to a fusing position after heating the selected wafer, wherein, in the fusing position, the selected wafer is disposed in contact with the first tube and the second tube.

18. The method of claim 17, further comprising:
 moving the selected wafer from the fusing position to the stand-by position.

19. The method of claim 18, further comprising:
 pressing the first tube against the second tube after the selected wafer is moved from the fusing position to the stand-by position fusing the first tube and the second tube together.

20. The method of claim 19, wherein moving the selected wafer from the stand-by position to the fusing position cuts the first tube and the second tube, and wherein prior to moving the selected wafer from the fusing position to the stand-by position, the method further comprises:
 rotating a first cut portion of the first tube and a first cut portion of the second tube disposed on a first side of the selected wafer relative to a second cut portion of the first tube and a second cut portion of the second tube disposed on a second side of the selected wafer, wherein the second side of the selected wafer is disposed opposite the first side of the selected wafer; and
 aligning the first cut portion of the first tube with the second cut portion of the second tube and the first cut portion of the second tube with the second cut portion of the first tube.

* * * * *